(12) United States Patent
Allen et al.

(10) Patent No.: US 9,175,246 B2
(45) Date of Patent: *Nov. 3, 2015

(54) FATTY AMINES, AMIDOAMINES, AND THEIR DERIVATIVES FROM NATURAL OIL METATHESIS

(75) Inventors: Dave R. Allen, Chicago, IL (US); Marcos Alonso, Chicago, IL (US); Randal J. Bernhardt, Antioch, IL (US); Aaron Brown, Chicago, IL (US); Kelly Buchek, Hoffman Estates, IL (US); Gary Luebke, Chicago, IL (US); Renee Luka, Park Ridge, IL (US); Andrew D. Malec, Chicago, IL (US); Ronald A. Masters, Glenview, IL (US); Lawrence A. Munie, Grayslake, IL (US); Dennis S. Murphy, Libertyville, IL (US); Irene Shapiro, Buffalo Grove, IL (US); Patti Skelton, Winder, GA (US); Brian Sook, Lawrenceville, GA (US); Michael R. Terry, Gurnee, IL (US); Laura Lee Whitlock, Highland Park, IL (US); Michael Wiester, Chicago, IL (US); Patrick Shane Wolfe, Palatine, IL (US)

(73) Assignee: Stepan Company, Northfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/878,981

(22) PCT Filed: Oct. 25, 2011

(86) PCT No.: PCT/US2011/057602
§ 371 (c)(1),
(2), (4) Date: May 15, 2013

(87) PCT Pub. No.: WO2012/061095
PCT Pub. Date: May 10, 2012

(65) Prior Publication Data
US 2013/0225408 A1 Aug. 29, 2013

Related U.S. Application Data

(60) Provisional application No. 61/406,570, filed on Oct. 25, 2010, provisional application No. 61/406,547, filed on Oct. 25, 2010, provisional application No. 61/406,556, filed on Oct. 25, 2010.

(51) Int. Cl.
| | | |
|---|---|---|
| *C07C 237/16* | (2006.01) | |
| *C07C 211/21* | (2006.01) | |
| *C07C 231/12* | (2006.01) | |
| *C07C 303/18* | (2006.01) | |

(Continued)

(52) U.S. Cl.
CPC . *C11C 3/08* (2013.01); *A01N 25/02* (2013.01); *A01N 25/04* (2013.01); *A01N 25/30* (2013.01); *A01N 33/12* (2013.01); *A01N 37/18* (2013.01); *A01N 37/44* (2013.01); *A01N 41/04* (2013.01); *A61K 8/416* (2013.01); *A61K 8/42* (2013.01); *A61K 8/44* (2013.01); *A61K 8/466* (2013.01); *A61K 8/92* (2013.01); *A61Q 5/12* (2013.01); *A61Q 19/10* (2013.01); *A62D 1/0071* (2013.01); *B01F 17/0028* (2013.01); *B01F 17/0057* (2013.01); *C07C 6/04* (2013.01); *C07C 41/03* (2013.01); *C07C 43/11* (2013.01); *C07C 67/26* (2013.01); *C07C 69/533* (2013.01); *C07C 69/593* (2013.01); *C07C 209/12* (2013.01); *C07C 211/21* (2013.01); *C07C 219/08* (2013.01); *C07C 231/12* (2013.01); *C07C 237/16* (2013.01); *C07C 303/18* (2013.01); *C08G 65/2615* (2013.01); *C08K 5/01* (2013.01); *C08K 5/20* (2013.01); *C11C 3/00* (2013.01); *C11D 1/002* (2013.01); *C11D 1/04* (2013.01); *C11D 1/28* (2013.01); *C11D 1/62* (2013.01); *C11D 1/74* (2013.01); *C11D 1/83* (2013.01); *C11D 1/92* (2013.01); *C11D 1/94* (2013.01);

(Continued)

(58) Field of Classification Search
USPC ............ 554/1, 35, 51, 52, 223; 514/601, 608, 514/673, 740; 564/123, 133, 134, 135, 137, 564/141, 193, 197, 198, 204, 509
See application file for complete search history.

(56) References Cited

U.S. PATENT DOCUMENTS

| | | |
|---|---|---|
| 2,653,970 A | 9/1953 | Fessler et al. |
| 2,865,968 A | 5/1955 | Hansley et al. |

(Continued)

FOREIGN PATENT DOCUMENTS

| | | | |
|---|---|---|---|
| DE | 2551483 A1 | 5/1977 | |
| JP | 4193025 B | * 1/2002 | |

(Continued)

OTHER PUBLICATIONS

Tetrahedron 68 2012 , 1117.

(Continued)

*Primary Examiner* — Jane C Oswecki
(74) *Attorney, Agent, or Firm* — Dilworth IP LLC

(57) ABSTRACT

Fatty amine compositions made from a metathesis-derived C10-C17 monounsaturated acid, octadecene-1,18-dioic acid, or their ester derivatives are disclosed. In another aspect, fatty amidoamines made by reacting a metathesis-derived C10-C17 monounsaturated acid, octadecene-1,18-dioic acid, or their ester derivatives with an aminoalkyl-substituted tertiary amine are disclosed. The fatty amines or amidoamines are advantageously sulfonated, sulfitated, oxidized, or reduced. In other aspects, the ester derivative is a modified triglyceride made by self-metathesis of a natural oil or an unsaturated triglyceride made by cross-metathesis of a natural oil with an olefin.

13 Claims, No Drawings

(51) Int. Cl.

| | |
|---|---|
| C11C 3/08 | (2006.01) |
| C11D 1/28 | (2006.01) |
| C11D 1/74 | (2006.01) |
| C11D 1/94 | (2006.01) |
| C08K 5/20 | (2006.01) |
| C07C 67/26 | (2006.01) |
| C07C 41/03 | (2006.01) |
| C07C 43/11 | (2006.01) |
| C07C 6/04 | (2006.01) |
| C07C 69/533 | (2006.01) |
| C07C 69/593 | (2006.01) |
| B01F 17/00 | (2006.01) |
| C11D 1/83 | (2006.01) |
| A01N 25/04 | (2006.01) |
| A01N 33/12 | (2006.01) |
| A01N 37/18 | (2006.01) |
| A01N 37/44 | (2006.01) |
| A01N 41/04 | (2006.01) |
| A61K 8/41 | (2006.01) |
| A61K 8/42 | (2006.01) |
| A61K 8/44 | (2006.01) |
| A61K 8/46 | (2006.01) |
| A61Q 5/12 | (2006.01) |
| A61Q 19/10 | (2006.01) |
| A62D 1/02 | (2006.01) |
| C11D 1/62 | (2006.01) |
| C11D 1/92 | (2006.01) |
| C11D 1/04 | (2006.01) |
| A01N 25/02 | (2006.01) |
| A61K 8/92 | (2006.01) |
| C08K 5/01 | (2006.01) |
| C11C 3/00 | (2006.01) |
| C11D 3/48 | (2006.01) |
| C07C 219/08 | (2006.01) |
| A01N 25/30 | (2006.01) |
| C07C 209/12 | (2006.01) |
| C11D 1/00 | (2006.01) |
| C08G 65/26 | (2006.01) |
| C07C 309/14 | (2006.01) |
| C11C 1/02 | (2006.01) |
| C09K 8/00 | (2006.01) |
| C09K 15/28 | (2006.01) |
| C11D 1/90 | (2006.01) |
| C11D 1/65 | (2006.01) |

(52) U.S. Cl.
CPC ... *C11D 3/48* (2013.01); *C09K 8/00* (2013.01); *C09K 15/28* (2013.01); *C11D 1/652* (2013.01); *C11D 1/90* (2013.01)

(56) References Cited

U.S. PATENT DOCUMENTS

| | | | |
|---|---|---|---|
| 3,169,142 A | 2/1965 | Knaggs et al. | |
| 3,193,586 A | 7/1965 | Rittmeister et al. | |
| 3,468,869 A | 9/1969 | Sherburne et al. | |
| 3,494,924 A | 2/1970 | Bonetti et al. | |
| 3,497,555 A | 2/1970 | Dudzinski et al. | |
| 3,539,601 A * | 11/1970 | Morton | 554/41 |
| 3,544,613 A | 12/1970 | Knaggs et al. | |
| 3,943,234 A | 3/1976 | Roggenkamp | |
| 4,087,457 A | 5/1978 | Convers et al. | |
| 4,148,821 A | 4/1979 | Nussbaum et al. | |
| 4,185,098 A | 1/1980 | Cuntze et al. | |
| 4,275,013 A | 6/1981 | Tokosh et al. | |
| 4,346,087 A | 8/1982 | Hamanaka et al. | |
| 4,409,399 A | 10/1983 | Swift et al. | |
| 4,545,941 A | 10/1985 | Rosenburg | |
| 4,594,455 A | 6/1986 | Dudzinski | |
| 4,714,610 A | 12/1987 | Gerstein | |
| 4,758,376 A * | 7/1988 | Hirota et al. | 510/467 |
| 4,994,622 A | 2/1991 | Fong et al. | |
| 5,124,491 A | 6/1992 | Fleckenstein et al. | |
| 5,167,864 A | 12/1992 | Borland et al. | |
| 5,211,883 A | 5/1993 | Yamashina et al. | |
| 5,226,943 A | 7/1993 | Hulshof | |
| 5,322,630 A | 6/1994 | Williams et al. | |
| 5,482,908 A | 1/1996 | Le-khac | |
| 5,556,615 A * | 9/1996 | Janchitraponvej et al. | 424/70.11 |
| 5,668,085 A | 9/1997 | Forbes et al. | |
| 5,696,294 A | 12/1997 | Abe et al. | |
| 5,840,985 A | 11/1998 | Nepras et al. | |
| 5,858,955 A * | 1/1999 | Stringer et al. | 510/417 |
| 6,107,498 A | 8/2000 | Maisonneuve et al. | |
| 6,110,886 A | 8/2000 | Scepanski | |
| 6,211,883 B1 * | 4/2001 | Goel | 345/423 |
| 6,239,093 B1 * | 5/2001 | Foley et al. | 510/352 |
| 6,683,224 B1 | 1/2004 | Hourticolon et al. | |
| 6,747,164 B2 | 6/2004 | Gustavsson et al. | |
| 7,208,643 B2 | 4/2007 | Namba et al. | |
| 7,244,698 B2 * | 7/2007 | Treybig et al. | 510/188 |
| 7,517,842 B2 * | 4/2009 | Barnhart et al. | 510/138 |
| 7,576,227 B2 | 8/2009 | Bicerano et al. | |
| 7,718,816 B2 * | 5/2010 | Yajima et al. | 554/35 |
| 7,960,599 B2 | 6/2011 | Millis et al. | |
| 8,067,610 B2 | 11/2011 | Schrodi | |
| 2005/0245772 A1 | 11/2005 | Fong et al. | |
| 2007/0010680 A1 | 1/2007 | Yajima et al. | |
| 2007/0093393 A1 | 4/2007 | Navarrete et al. | |
| 2007/0118916 A1 | 5/2007 | Puzio et al. | |
| 2008/0033026 A1 | 2/2008 | Zullo et al. | |
| 2009/0264672 A1 | 10/2009 | Abraham et al. | |
| 2009/0305938 A1 | 12/2009 | Assmann et al. | |
| 2010/0056375 A1 | 3/2010 | Jonsson et al. | |
| 2010/0120658 A1* | 5/2010 | Schiedel et al. | 510/515 |
| 2010/0145086 A1 | 6/2010 | Schrodi et al. | |
| 2010/0184855 A1 | 7/2010 | Bernhardt et al. | |
| 2010/0282467 A1 | 11/2010 | Hutchison et al. | |
| 2011/0113679 A1 | 5/2011 | Cohen et al. | |
| 2011/0210028 A1 | 9/2011 | Zhu | |
| 2011/0313180 A1 | 12/2011 | Uptain et al. | |
| 2012/0071676 A1 | 3/2012 | Schrodi et al. | |
| 2012/0197031 A1 | 8/2012 | Firth et al. | |
| 2013/0035502 A1 | 2/2013 | Cohen et al. | |
| 2013/0035532 A1 | 2/2013 | Schrodi | |

FOREIGN PATENT DOCUMENTS

| | | | |
|---|---|---|---|
| JP | 4273853 B * | 6/2003 | |
| JP | 4969782 B * | 7/2004 | |
| WO | 200704922 A1 | 7/2007 | |
| WO | WO-2008048522 | 4/2008 | |

OTHER PUBLICATIONS

Appl. Catal.A. 346 2009, 158.
J.C. Mol., Topics in Catalysis 27 2004, 97.
J. C. Mol., Green Chem., 4 2002, 5.
Smith, M.B. et al., "March's Advanced Organic Chemistry", 5th ed. 1541, 2001, 1549-1550.
Larock, "Comprehensive Organic Transformations", 1989, 432-434.
J. Barrault, Catal. Today 37 (1997) 137.
Shelley et al. "Ein allgemein einsetzbares, mildes Eintopfverfahren zur Umwandlung von Amiden in Aldehyde", Angew. Chem, vol. 108, No. 13-14, (Jul. 15, 1996) pp. 1662-1664.
Besson et al. "Synthesis of Allylic Amines Through the Palladium-Catalyzed Hydroamination of Allenes", Tetrahedron. Lett., vol. 36, No. 22, (May 29, 1995), pp. 3857-3860.
Cheng et al. "Efficient, asymmetric synthesis of (-)-isooncinotine" Tetrahedron, vol. 63, No. 14 (Mar. 9, 2007) pp. 3000-3005.
Extended European Search Report in EP Application 11838500.4 completed on Oct. 1, 2014.
Bower; Angew. Chem. 108 (1996) 1662.

* cited by examiner

FATTY AMINES, AMIDOAMINES, AND THEIR DERIVATIVES FROM NATURAL OIL METATHESIS

FIELD OF THE INVENTION

The invention relates to fatty amines, amidoamines, and derivative compositions that originate from natural resources, particularly natural oils and their metathesis products.

BACKGROUND OF THE INVENTION

"Fatty amines" generally have a nonpolar chain of six or more carbons, typically 6-30 carbons, and at least one polar end group comprising or derived from an amine, for example, a tertiary amine. Fatty amines have value in and of themselves, or they can be modified to provide different utility. For instance, oxidation of a tertiary amine group provides an amine oxide with properties unlike the free amine. A variety of quaternization methods further expand the utility of fatty tertiary amines as intermediate targets.

Fatty amines and/or their derivatives have been used in a wide range of end-use applications, including fabric softening or other antistatic uses (see U.S. Pat. Nos. 3,468,869; 3,943,234; and 6,110,886), shampoos and hair conditioning (U.S. Pat. Nos. 4,714,610 and 5,167,864), cleaners and detergents including hard surface cleaners (U.S. Pat. No. 5,858,955 and U.S. Pat. Appl. Publ. Nos. 2010/0184855 and 2009/0305938), corrosion inhibitors (U.S. Pat. No. 5,322,630), and agricultural surfactants (U.S. Pat. Nos. 5,226,943 and 5,668,085).

Fatty tertiary amines can be made by converting fatty esters or acids with a secondary amine to the amide derivative, followed by reduction of the carbonyl to give a terminal tertiary amine. In a preferred approach, the reduction step is avoided by reacting a fatty ester with an aminoalkyl-substituted tertiary amine. For instance, N,N-dimethyl-1,3-propanediamine (DMAPA) reacts with a fatty methyl ester, triglyceride or fatty acid to give a fatty amidoamine. The amidoamine has a terminal tertiary amine group that is well suited to further functionalization by oxidation or quaternization.

Fatty amines can also be made by direct amination of fatty alcohols, usually with a copper and/or nickel-based catalyst (see, e.g., U.S. Pat. Nos. 3,497,555; 4,594,455; and 4,994,622), or in multiple steps from the fatty alcohol by first converting the alcohol to a halide, sulfonate ester, or the like, and then reacting with ammonia or a primary or secondary amine.

The fatty acids or esters used to make fatty amines and their derivatives are usually made by hydrolysis or transesterification of triglycerides, which are typically animal or vegetable fats. Consequently, the fatty portion of the acid or ester will typically have 6-22 carbons with a mixture of saturated and internally unsaturated chains. Depending on source, the fatty acid or ester often has a preponderance of $C_{16}$ to $C_{22}$ component. For instance, methanolysis of soybean oil provides the saturated methyl esters of palmitic ($C_{16}$) and stearic ($C_{18}$) acids and the unsaturated methyl esters of oleic ($C_{18}$ mono-unsaturated), linoleic ($C_{18}$ di-unsaturated), and α-linolenic ($C_{18}$ tri-unsaturated) acids. The unsaturation in these acids has either exclusively or predominantly cis-configuration.

Recent improvements in metathesis catalysts (see J. C. Mol, *Green Chem.* 4 (2002) 5) provide an opportunity to generate reduced chain length, monounsaturated feedstocks, which are valuable for making detergents and surfactants, from $C_{16}$ to $C_{22}$-rich natural oils such as soybean oil or palm oil. Soybean oil and palm oil can be more economical than, for example, coconut oil, which is a traditional starting material for making detergents. As Professor Mol explains, metathesis relies on conversion of olefins into new products by rupture and reformation of carbon-carbon double bonds mediated by transition metal carbene complexes. Self-metathesis of an unsaturated fatty ester can provide an equilibrium mixture of starting material, an internally unsaturated hydrocarbon, and an unsaturated diester. For instance, methyl oleate (methyl cis-9-octadecenoate) is partially converted to 9-octadecene and dimethyl 9-octadecene-1,18-dioate, with both products consisting predominantly of the trans-isomer. Metathesis effectively isomerizes the cis-double bond of methyl oleate to give an equilibrium mixture of cis- and trans-isomers in both the "unconverted" starting material and the metathesis products, with the trans-isomers predominating.

Cross-metathesis of unsaturated fatty esters with olefins generates new olefins and new unsaturated esters that can have reduced chain length and that may be difficult to make otherwise. For instance, cross-metathesis of methyl oleate and 3-hexene provides 3-dodecene and methyl 9-dodecenoate (see also U.S. Pat. No. 4,545,941). Terminal olefins are particularly desirable synthetic targets, and Elevance Renewable Sciences, Inc. recently described an improved way to prepare them by cross-metathesis of an internal olefin and an α-olefin in the presence of a ruthenium alkylidene catalyst (see U.S. Pat. Appl. Publ. No. 2010/0145086). A variety of cross-metathesis reactions involving an α-olefin and an unsaturated fatty ester (as the internal olefin source) are described. Thus, for example, reaction of soybean oil with propylene followed by hydrolysis gives, among other things, 1-decene, 2-undecenes, 9-decenoic acid, and 9-undecenoic acid. Despite the availability (from cross-metathesis of natural oils and olefins) of unsaturated fatty esters having reduced chain length and/or predominantly trans-configuration of the unsaturation, fatty amines and their derivatives made from these feedstocks appear to be unknown. Moreover, fatty amines and their derivatives have not been made from the $C_{18}$ unsaturated diesters that can be made readily by self-metathesis of a natural oil.

In sum, traditional sources of fatty acids and esters used for making fatty amines and their derivatives generally have predominantly (or exclusively) cis-isomers and lack relatively short-chain (e.g., $C_{10}$ or $C_{12}$) unsaturated fatty portions. Metathesis chemistry provides an opportunity to generate precursors having shorter chains and mostly trans-isomers, which could impart improved performance when the precursors are converted to downstream compositions (e.g., in surfactants). New $C_{18}$ difunctional fatty amines and derivatives are also potentially available from oil or $C_{10}$ unsaturated acid or ester self-metathesis. In addition to an expanded variety of precursors, the unsaturation present in the precursors allows for further functionalization, e.g., by sulfonation or sulfitation.

SUMMARY OF THE INVENTION

In one aspect, the invention relates to fatty amine compositions. The fatty amines are made from a metathesis-derived $C_{10}$-$C_{17}$ monounsaturated acid, octadecene-1,18-dioic acid, or their ester derivatives. The fatty amines can be made in several ways. In one synthetic approach, the metathesis-derived acid or ester is reacted with ammonia or a primary or secondary amine, and the resulting fatty amide is reduced to give the fatty amine. In another approach, the metathesis-derived acid or ester is reduced to give a fatty alcohol, and the fatty alcohol is aminated in a single or multiple steps.

In another aspect, the invention relates to fatty amidoamines made by reacting a metathesis-derived $C_{10}$-$C_{17}$ monounsaturated acid, octadecene-1,18-dioic acid, or their ester derivatives with an aminoalkyl-substituted tertiary amine such as DMAPA.

The invention includes derivatives made by sulfonating, sulfitating, or oxidizing the fatty amines or amidoamines.

In one aspect, the ester derivative of the $C_{10}$-$C_{17}$ monounsaturated acid or octadecene-1,18-dioic acid is a lower alkyl ester. In other aspects, the ester derivative is a modified triglyceride made by self-metathesis of a natural oil or an unsaturated triglyceride made by cross-metathesis of a natural oil with an olefin.

Fatty amines and amidoamines and their derivatives are valuable for a wide variety of end uses, including cleaners, fabric treatment, hair conditioning, personal care (liquid cleansing products, conditioning bars, oral care products), antimicrobial compositions, agricultural uses, and oil field applications.

DETAILED DESCRIPTION OF THE INVENTION

In one aspect, the invention relates to fatty amines made from a metathesis-derived $C_{10}$-$C_{17}$ monounsaturated acid, octadecene-1,18-dioic acid, or their ester derivatives.

The $C_{10}$-$C_{17}$ monounsaturated acid, octadecene-1,18-dioic acid, or their ester derivatives used as a reactant is derived from metathesis of a natural oil. Traditionally, these materials, particularly the short-chain acids and derivatives (e.g., 9-decylenic acid or 9-dodecylenic acid) have been difficult to obtain except in lab-scale quantities at considerable expense. However, because of the recent improvements in metathesis catalysts, these acids and their ester derivatives are now available in bulk at reasonable cost. Thus, the $C_{10}$-$C_{17}$ monounsaturated acids and esters are conveniently generated by cross-metathesis of natural oils with olefins, preferably α-olefins, and particularly ethylene, propylene, 1-butene, 1-hexene, 1-octene, and the like. Self-metathesis of the natural oil or a $C_{10}$ acid or ester precursor (e.g., methyl 9-decenoate) provides the $C_{18}$ diacid or diester in optimal yield when it is the desired product.

Preferably, at least a portion of the $C_{10}$-$C_{17}$ monounsaturated acid has "$\Delta^9$" unsaturation, i.e., the carbon-carbon double bond in the $C_{10}$-$C_{17}$ acid is at the 9-position with respect to the acid carbonyl. In other words, there are preferably seven carbons between the acid carbonyl group and the olefin group at C9 and C10. For the $C_{11}$ to $C_{17}$ acids, an alkyl chain of 1 to 7 carbons, respectively is attached to C10. Preferably, the unsaturation is at least 1 mole % trans-$\Delta^9$, more preferably at least 25 mole % trans-$\Delta^9$, more preferably at least 50 mole % trans-$\Delta^9$, and even more preferably at least 80% trans-$\Delta^9$. The unsaturation may be greater than 90 mole %, greater than 95 mole %, or even 100% trans-$\Delta^9$. In contrast, naturally sourced fatty acids that have $\Delta^9$ unsaturation, e.g., oleic acid, usually have ~100% cis-isomers.

Although a high proportion of trans-geometry (particularly trans-$\Delta^9$ geometry) may be desirable in the metathesis-derived fatty amines and derivatives of the invention, the skilled person will recognize that the configuration and the exact location of the carbon-carbon double bond will depend on reaction conditions, catalyst selection, and other factors. Metathesis reactions are commonly accompanied by isomerization, which may or may not be desirable. See, for example, G. Djigoué and M. Meier, *Appl. Catal. A: General* 346 (2009) 158, especially FIG. 3. Thus, the skilled person might modify the reaction conditions to control the degree of isomerization or alter the proportion of cis- and trans-isomers generated. For instance, heating a metathesis product in the presence of an inactivated metathesis catalyst might allow the skilled person to induce double bond migration to give a lower proportion of product having trans-$\Delta^9$ geometry.

An elevated proportion of trans-isomer content (relative to the usual all-cis configuration of the natural monounsaturated acid or ester) imparts different physical properties to fatty amine compositions made from them, including, for example, modified physical form, melting range, compactability, and other important properties. These differences should allow formulators that use fatty amines and their amine oxide derivatives greater latitude or expanded choice as they use the fatty amines or derivatives in cleaners, fabric treatment, personal care, agricultural uses, and other end uses.

Suitable metathesis-derived $C_{10}$-$C_{17}$ monounsaturated acids include, for example, 9-decylenic acid (9-decenoic acid), 9-undecenoic acid, 9-dodecylenic acid (9-dodecenoic acid), 9-tridecenoic acid, 9-tetradecenoic acid, 9-pentadecenoic acid, 9-hexadecenoic acid, 9-heptadecenoic acid, and the like, and their ester derivatives.

Usually, cross-metathesis or self-metathesis of the natural oil is followed by separation of an olefin stream from a modified oil stream, typically by distilling out the more volatile olefins. The modified oil stream is then reacted with a lower alcohol, typically methanol, to give glycerin and a mixture of alkyl esters. This mixture normally includes saturated $C_6$-$C_{22}$ alkyl esters, predominantly $C_{16}$-$C_{18}$ alkyl esters, which are essentially spectators in the metathesis reaction. The rest of the product mixture depends on whether cross- or self-metathesis is used. When the natural oil is self-metathesized and then transesterified, the alkyl ester mixture will include a $C_{18}$ unsaturated diester. When the natural oil is cross-metathesized with an α-olefin and the product mixture is transesterified, the resulting alkyl ester mixture includes a $C_{10}$ unsaturated alkyl ester and one or more $C_{11}$ to $C_{17}$ unsaturated alkyl ester coproducts in addition to the glycerin by-product. The terminally unsaturated $C_{10}$ product is accompanied by different coproducts depending upon which α-olefin(s) is used as the cross-metathesis reactant. Thus, 1-butene gives a $C_{12}$ unsaturated alkyl ester, 1-hexene gives a $C_{14}$ unsaturated alkyl ester, and so on. As is demonstrated in the examples below, the $C_{10}$ unsaturated alkyl ester is readily separated from the $C_{11}$ to $C_{17}$ unsaturated alkyl ester and each is easily purified by fractional distillation. These alkyl esters are excellent starting materials for making the inventive fatty amine compositions.

Natural oils suitable for use as a feedstock to generate the $C_{10}$-$C_{17}$ monounsaturated acid, octadecene-1,18-dioic acid, or their ester derivatives from self-metathesis or cross-metathesis with olefins are well known. Suitable natural oils include vegetable oils, algal oils, animal fats, tall oils, derivatives of the oils, and combinations thereof. Thus, suitable natural oils include, for example, soybean oil, palm oil, rapeseed oil, coconut oil, palm kernel oil, sunflower oil, safflower oil, sesame oil, corn oil, olive oil, peanut oil, cottonseed oil, canola oil, castor oil, tallow, lard, poultry fat, fish oil, and the like. Soybean oil, palm oil, rapeseed oil, and mixtures thereof are preferred natural oils.

Genetically modified oils, e.g., high-oleate soybean oil or genetically modified algal oil, can also be used. Preferred natural oils have substantial unsaturation, as this provides a reaction site for the metathesis process for generating olefins. Particularly preferred are natural oils that have a high content of unsaturated fatty groups derived from oleic acid. Thus, particularly preferred natural oils include soybean oil, palm oil, algal oil, and rapeseed oil.

A modified natural oil, such as a partially hydrogenated vegetable oil, can be used instead of or in combination with the natural oil. When a natural oil is partially hydrogenated, the site of unsaturation can migrate to a variety of positions on the hydrocarbon backbone of the fatty ester moiety. Because of this tendency, when the modified natural oil is self-metathesized or is cross-metathesized with the olefin, the reaction products will have a different and generally broader distribution compared with the product mixture generated from an unmodified natural oil. However, the products generated from the modified natural oil are similarly converted to inventive fatty amine or amidoamine compositions.

An alternative to using a natural oil as a feedstock to generate the $C_{10}$-$C_{17}$ monounsaturated acid, octadecene-1,18-dioic acid, or their ester derivatives from self-metathesis or cross-metathesis with olefins is a monounsaturated fatty acid obtained by the hydrolysis of a vegetable oil or animal fat, or an ester or salt of such an acid obtained by esterification of a fatty acid or carboxylate salt, or by transesterification of a natural oil with an alcohol. Also useful as starting compositions are polyunsaturated fatty esters, acids, and carboxylate salts. The salts can include an alkali metal (e.g., Li, Na, or K); an alkaline earth metal (e.g., Mg or Ca); a Group 13-15 metal (e.g., B, Al, Sn, Pb, or Sb), or a transition, lanthanide, or actinide metal. Additional suitable starting compositions are described at pp. 7-17 of PCT application WO 2008/048522, the contents of which are incorporated by reference herein.

The other reactant in the cross-metathesis reaction is an olefin. Suitable olefins are internal or α-olefins having one or more carbon-carbon double bonds. Mixtures of olefins can be used. Preferably, the olefin is a monounsaturated $C_2$-$C_{10}$ α-olefin, more preferably a monounsaturated $C_2$-$C_8$ α-olefin. Preferred olefins also include $C_4$-$C_9$ internal olefins. Thus, suitable olefins for use include, for example, ethylene, propylene, 1-butene, cis- and trans-2-butene, 1-pentene, isohexylene, 1-hexene, 3-hexene, 1-heptene, 1-octene, 1-nonene, 1-decene, and the like, and mixtures thereof.

Cross-metathesis is accomplished by reacting the natural oil and the olefin in the presence of a homogeneous or heterogeneous metathesis catalyst. The olefin is omitted when the natural oil is self-metathesized, but the same catalyst types are generally used. Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

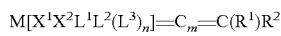

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is party of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

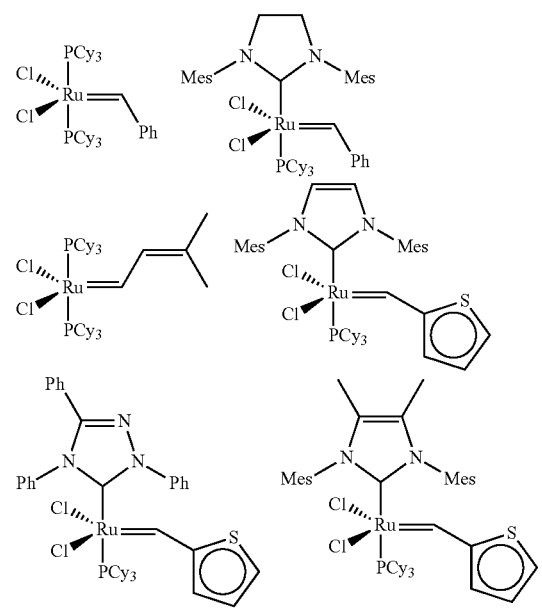

Heterogeneous catalysts suitable for use in the self- or cross-metathesis reaction include certain rhenium and molybdenum compounds as described, e.g., by J. C. Mol in Green Chem. 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. No. 4,545,941, the teachings of which are incorporated herein by reference, and references cited therein.

Fatty amines of the invention can be made by reacting a metathesis-derived $C_{10}$-$C_{17}$ monounsaturated acid, octadecene-1,18-dioic acid, or their ester derivatives with ammonia or a primary or secondary amine, followed by reduction of the resulting fatty amide. They can also be made reducing a metathesis-derived acid or ester derivative to a fatty alcohol, followed by amination of the fatty alcohol. Thus, intermediates to the inventive fatty amines are metathesis-derived fatty alcohols or fatty amides.

In one aspect, the ester derivative is a lower alkyl ester, especially a methyl ester. The lower alkyl esters are preferably generated by transesterifying a metathesis-derived triglyceride. For example, cross-metathesis of a natural oil with an olefin, followed by removal of unsaturated hydrocarbon metathesis products by stripping, and then transesterification of the modified oil component with a lower alkanol under basic conditions provides a mixture of unsaturated lower alkyl esters. The unsaturated lower alkyl ester mixture can be used "as is" to make the intermediates for the inventive fatty amines or it can be purified to isolate particular alkyl esters prior to making the intermediates.

In another aspect, the ester derivative is the metathesis-derived triglyceride discussed in the preceding paragraph. Instead of transesterifying the metathesis-derived triglyceride with a lower alkanol to generate lower alkyl esters as described above, the metathesis-derived triglyceride, following olefin stripping, is reacted directly with ammonia or a primary or secondary amine to make a fatty amide mixture, which is then reduced to give the inventive fatty amine mixture. Alternatively, the metathesis-derived triglyceride, following olefin stripping, is reduced to give a fatty alcohol mixture, which is then aminated to give the inventive fatty amine mixture.

The skilled person will appreciate that "ester derivative" here encompasses other acyl equivalents, such as acid chlorides, acid anhydrides, or the like, in addition to the lower alkyl esters and glyceryl esters discussed above.

In one synthetic approach, the metathesis-derived acid or ester derivative is reacted with ammonia or a primary or secondary amine to give a fatty amide, followed by reduction of the fatty amide to give the fatty amine.

Secondary amines are preferred reactants. Suitable secondary amines have a hydrogen and two hydrocarbyl groups attached to nitrogen. The hydrocarbyl groups are preferably saturated or unsaturated linear, branched, or cyclic $C_1$-$C_{20}$ alkyl, $C_6$-$C_{20}$ aryl, or $C_7$-$C_{20}$ arylalkyl. More preferably, both of the hydrocarbyl groups are $C_1$-$C_6$ alkyl groups. Suitable secondary amines include, for example, N,N-dimethylamine, N,N-diethylamine, N,N,-dipropylamine, N,N-diisopropylamine, N,N-dibutylamine, N-methyl-N-cyclohexylamine, N-methyl-N-phenylamine, N-methyl-N-benzylamine, or the like, and mixtures thereof. N,N-Dimethylamine is cost-effective and is particularly preferred.

Suitable amines include etheramines. Thus, amines that are reaction products of ammonia or primary amines and an alkylene oxide, for example 0.1 to 20 molar equivalents of ethylene oxide, propylene oxide, or the like, can be used. The amine can be, for instance, a monoalkylated derivative of a Jeffamine® M series polyether amine (product of Huntsman). In some instances of using an etheramine, it may be necessary to mask any hydroxyl functionality as an appropriate derivative, either before or after formation of the amide, so as to enable the subsequent reduction of this amide.

Although the fatty amides are made using a well-known process, the product mixture is unique because of the unconventional starting mixture of acid or ester derivatives. The reactants are typically heated, with or without a catalyst under conditions effective to convert the starting acid, ester, or other derivative to an amide. The reaction temperature is typically within the range of 40° C. to 300° C., preferably from 50° C. to 250° C., and more preferably from 50° C. to 200° C.

Reduction of the fatty amide to give a terminal amine is accomplished using well-known methods, including reactions with a hydride reducing agent (boranes, aluminum hydrides, borohydrides, or the like), or catalytic hydrogenation. Suitable reducing reagents include, for example, borane, borane dimethylsulfide, sodium borohydride/iodine, lithium cyanoborohydride, aluminum hydride, lithium aluminum hydride, diisobutylaluminum hydride, and the like. For additional examples, see R. Larock, *Comprehensive Organic Transformations: A Guide to Functional Group Preparations* (1989), pp. 432-434, and M. Smith and J. March, *March's Advanced Organic Chemistry*, 5$^{th}$ ed. (2001), pp. 1549-1550.

In an alternative synthetic approach, the fatty amine is made by first reducing the metathesis-derived acid or ester derivative to give a fatty alcohol, followed by amination of the fatty alcohol. The metathesis-derived acid or ester derivative is reduced to a fatty alcohol using a metal hydride reagent (sodium borohydride, lithium aluminum hydride, or the like), catalytic hydrogenation, or other well-known techniques for generating the fatty alcohol (see, e.g., U.S. Pat. Nos. 2,865,968; 3,193,586; 5,124,491; 6,683,224; and 7,208,643, the teachings of which are incorporated herein by reference). Amination is then preferably performed in a single step by reacting the fatty alcohol with ammonia or a primary or secondary amine in the presence of an amination catalyst. Suitable amination catalysts are well known. Catalysts comprising copper, nickel, and/or alkaline earth metal compounds are common. For suitable catalysts and processes for amination, see U.S. Pat. Nos. 5,696,294; 4,994,622; 4,594,455; 4,409,399; and 3,497,555, the teachings of which are incorporated herein by reference.

In a preferred aspect of the invention, the fatty amine is a fatty amidoamine made by reacting a metathesis-derived $C_{10}$-$C_{17}$ monounsaturated acid, octadecene-1,18-dioic acid, or their ester derivatives with an aminoalkyl-substituted tertiary amine. This provides a product having tertiary amine functionality without the need to reduce a fatty amide to a fatty amine with a strong reducing agent. Suitable aminoalkyl-substituted tertiary amines have a primary amino group at one terminus, an alkylene group, and a tertiary amine group at the other end of the molecule. The alkylene group is preferably a $C_2$-$C_6$ linear or branched diradical such as ethylene, propylene, butylene, or the like. Thus, suitable aminoalkyl-substituted tertiary amines include, for example, N,N-dimethyl-1,2-ethanediamine, N,N-dimethyl-1,3-propanediamine (DMAPA), N,N-diethyl-1,3-propanediamine, N,N-dimethyl-1,4-butanediamine, and the like. DMAPA is particularly preferred. The primary amine group exhibits good reactivity with the acid or ester derivative, while the terminal tertiary amine is preserved in the product and provides a site for further modification or functionalization. The obtained tertiary amine is readily transformed, for example, into an amine oxide, betaine, sulfobetaine, or quaternary ammonium group.

The relative amounts of amine, ammonia, or aminoalkyl-substituted tertiary amine that is reacted with the ester or acid reactants depends on the desired stoichiometry and is left to the skilled person's discretion. In general, enough of the amine (or aminoalkyl-substituted tertiary amine) is used to react with most or all of the available acid or ester groups, i.e., preferably greater than 90%, and more preferably greater than 95%, of the available acid or ester groups.

Some fatty amines have the formula:

where:
$R^1$ is —$C_{10}H_{18}$—$R^4$ or —$C_{18}H_{34}$—$NR^2R^3$; each of $R^2$ and $R^3$ is independently hydrogen, substituted or unsubstituted alkyl, aryl, alkenyl, oxyalkylene, or polyoxyalkylene; and $R^4$ is hydrogen or $C_1$-$C_7$ alkyl. Preferably, $R^1$ is —$(CH_2)_8$—CH=$CHR^4$ or —$(CH_2)_8$—CH=CH—$(CH_2)_8$—$NR^2R^3$.

Some fatty amidoamines have the formula:

$R^3(R^2)N(CH_2)_nNH(CO)R^1$ where:
$R^1$ is —$C_9H_{16}$—$R^4$ or —$C_{16}H_{30}$—(CO)$NH(CH_2)_nN(R^2)R^3$; each of $R^2$ and $R^3$ is independently substituted or unsubstituted alkyl, aryl, alkenyl, oxyalkylene, or polyoxyalkylene; $R^4$ is hydrogen or $C_1$-$C_7$ alkyl; and n=2-8. Preferably, $R^1$ is

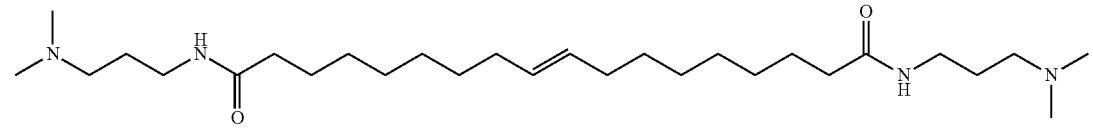

—$(CH_2)_7$—CH=$CHR^4$ or —$(CH_2)_7$—CH=CH—$(CH_2)_7$—(CO)$NH(CH_2)_nN(R)R^3$.

General Note Regarding Chemical Structures:

As the skilled person will recognize, products made in accordance with the invention are typically mixtures of cis- and trans-isomers. Except as otherwise indicated, all of the structural representations provided herein show only a trans-isomer. The skilled person will understand that this convention is used for convenience only, and that a mixture of cis- and trans-isomers is understood unless the context dictates otherwise. (The "C18-" series of products in the examples below, for instance, are nominally 100% trans-isomers whereas the "Mix-" series are nominally 80:20 trans-/cis-isomer mixtures.) Structures shown often refer to a principal product that may be accompanied by a lesser proportion of other components or positional isomers. For instance, reaction products from modified triglycerides are complex mixtures. As another example, sulfonation or sulfitation processes often give mixtures of sultones, alkanesulfonates, and alkenesulfonates, in addition to isomerized products. Thus, the structures provided represent likely or predominant products. Charges may or may not be shown but are understood, as in the case of amine oxide structures. Counterions, as in quaternized compositions, are not usually included, but they are understood by the skilled person from the context.

Specific examples of $C_{10}$, $C_{12}$, $C_{14}$, and $C_{16}$-based fatty amines and fatty amidoamines appear below:

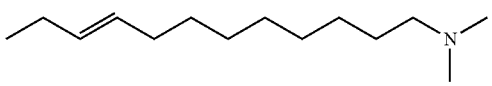

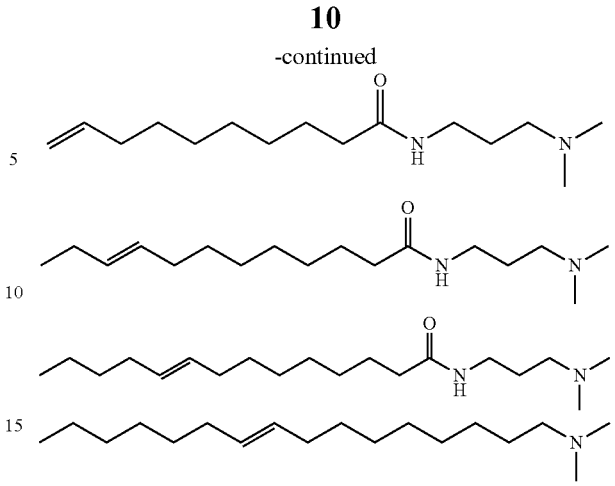

An exemplary $C_{18}$-based fatty amidoamine:

The fatty amine or fatty amidoamine product mixture can be complex when the ester derivative reacted with the amine or aminoalkyl-substituted tertiary amine is a modified triglyceride made by self-metathesis of a natural oil and separation to remove olefins (see, e.g., the MTG and PMTG products described below) or an unsaturated triglyceride made by cross-metathesis of a natural oil and an olefin and separation to remove olefins (see, e.g., the UTG and PUTG products described below). As is evident from the reaction schemes, the MTG and PMTG products from DMAPA include an unsaturated $C_{18}$ diamidoamine as a principal component, while the UTG and PUTG products include a $C_{10}$ unsaturated amidoamine component and one or more $C_{11}$ to $C_{17}$ unsaturated amidoamine components. (For example, with 1-butene as the cross-metathesis reactant, as illustrated, a $C_{12}$ unsaturated amidoamine component results.) Other components of the product mixtures are glycerin and saturated or unsaturated amides that incorporate DMAPA. Despite the complexity, purification to isolate a particular species is often neither economical nor desirable for good performance.

Thus, in one aspect, the fatty amidoamine is produced by reacting an aminoalkyl-substituted tertiary amine with a modified triglyceride made by self-metathesis of a natural oil. Self-metathesis of the natural oil provides a mixture of olefins and a modified triglyceride that is enriched in a $C_{18}$ unsaturated diester component along with $C_{16}$-$C_{18}$ saturated diesters. The olefins are stripped out, usually with heat and reduced pressure. When the modified triglyceride is reacted directly with DMAPA, a complex mixture results in which primary amino groups of DMAPA completely or partially displace glycerin from the glyceryl esters to form amidoamine functionalities. Representative amidoamine products below are made by reacting DMAPA with MTG-0 (modified triglyceride from soybean oil) or PMTG-0 (modified triglyceride from palm oil). One example is the MTG DMAPA amide ("MTG-5"):

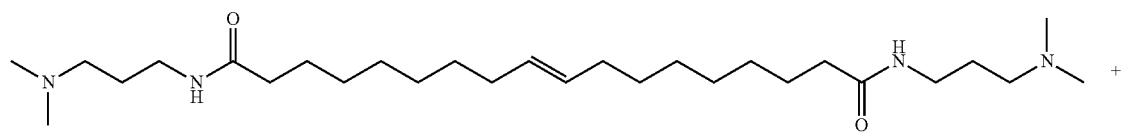

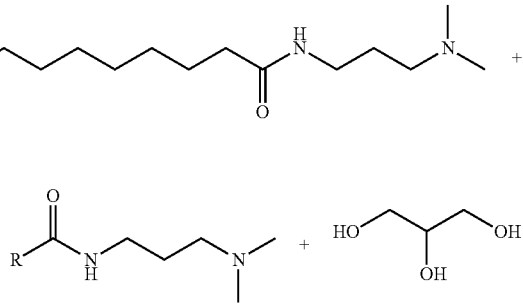

R = C16, C18 Sat. + Unsat.

In another aspect, the fatty amidoamine is produced by reacting an aminoalkyl-substituted tertiary amine with an unsaturated triglyceride made by cross-metathesis of a natural oil with an olefin. Cross-metathesis of the natural oil and olefin provides a mixture of olefins and an unsaturated triglyceride that is rich in $C_{10}$ and $C_{12}$ unsaturated esters as well as $C_{16}$-$C_{18}$ saturated esters. The olefins are stripped out, usually with heat and reduced pressure. When the unsaturated triglyceride is reacted directly with DMAPA, a complex mixture results in which primary amino groups of DMAPA completely or partially displace glycerin from the glyceryl esters to form amidoamine functionalities. Representative amidoamine products below are made by reacting DMAPA with UTG-0 (unsaturated triglyceride from cross-metathesis of soybean oil and 1-butene) or PUTG-0 (unsaturated triglyceride from cross-metathesis of palm oil with 1-butene). One example is the PUTG DMAPA amide product ("PUTG-5"):

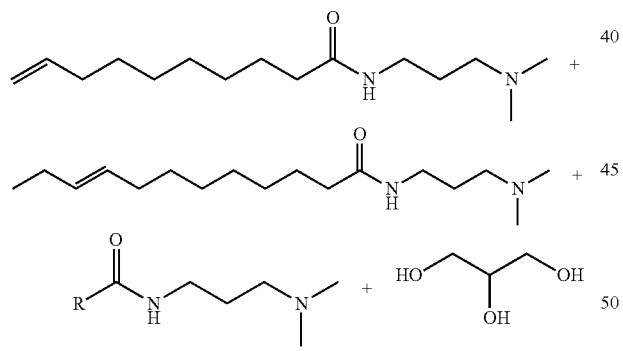

R = C16, C18 Sat.

The reaction to form the amidoamines from lower alkyl esters can be performed under a nitrogen sparge or under vacuum to remove liberated alcohol. When glyceride esters are reactants, the liberated glycerin need not be removed from the product. The reaction is considered complete when the residual glyceride content of the product reaches the desired level.

The invention includes derivatives made by one or more of oxidizing, sulfonating, and sulfitating the fatty amine or fatty amidoamine. If desired, the carbonyl group of fatty amidoamines can also be reduced to give fatty amines.

Oxidation is accomplished by reacting the fatty amine or fatty amidoamine with on oxidant such as hydrogen peroxide, air, ozone, organic hydroperoxides, or the like, to covert a tertiary amine group to an amine oxide functionality according to well-known methods (see *March's Advanced Organic Chemistry*, supra, at, p. 1541 and U.S. Pat. No. 3,494,924). Exemplary procedures for oxidizing fatty amines or fatty amidoamines to the corresponding oxides using hydrogen peroxide also appear below.

Examples of suitable $C_{10}$, $C_{12}$, $C_{14}$, and $C_{16}$-based amine oxides:

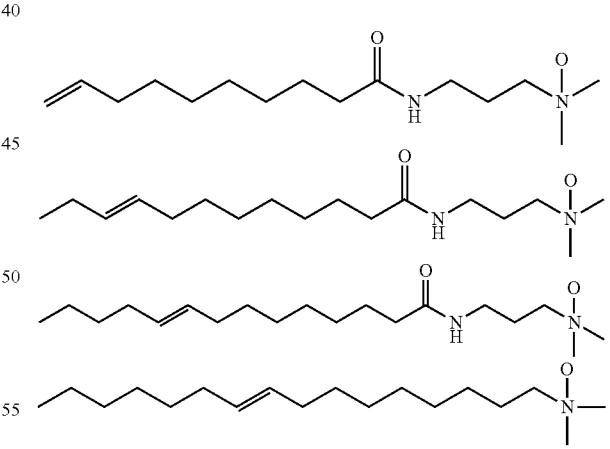

An exemplary $C_{18}$-based amine oxide:

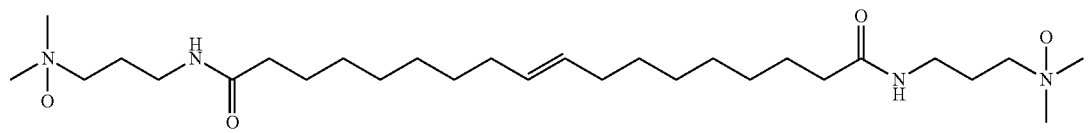

An exemplary amine oxide based on a PUTG-based amidoamine mixture ("PUTG-12"):

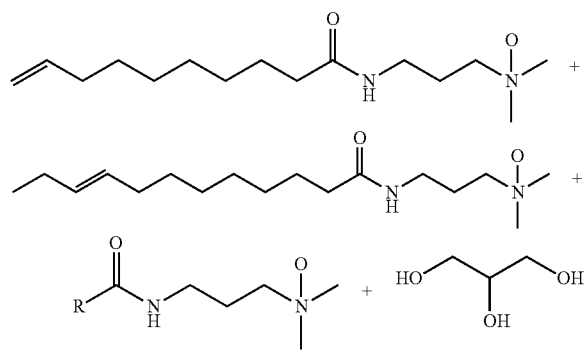

R = C16, C18 Sat.

The fatty amines or amidoamines and their derivatives have unsaturation that can be sulfonated or sulfitated if desired. Sulfonation is performed using well-known methods, including reacting the olefin with sulfur trioxide. Sulfonation may optionally be conducted using an inert solvent. Non-limiting examples of suitable solvents include liquid $SO_2$, hydrocarbons, and halogenated hydrocarbons. In one commercial approach, a falling film reactor is used to continuously sulfonate the olefin using sulfur trioxide. Other sulfonating agents can be used with or without use of a solvent (e.g., chlorosulfonic acid, fuming sulfuric acid), but sulfur trioxide is generally the most economical. The sultones that are the immediate products of reacting olefins with $SO_3$, chlorosulfonic acid, and the like may be subsequently subjected to a hydrolysis reaction with aqueous caustic to afford mixtures of alkene sulfonates and hydroxyalkane sulfonates. Suitable methods for sulfonating olefins are described in U.S. Pat. Nos. 3,169,142; 4,148,821; and U.S. Pat. Appl. Publ. No. 2010/0282467, the teachings of which are incorporated herein by reference.

Sulfitation is accomplished by combining an olefin in water (and usually a cosolvent such as isopropanol) with at least a molar equivalent of a sulfitating agent using well-known methods. Suitable sulfitating agents include, for example, sodium sulfite, sodium bisulfite, sodium metabisulfite, or the like. Optionally, a catalyst or initiator is included, such as peroxides, iron, or other free-radical initiators. Typically, the reaction mixture is conducted at 15-100° C. until the reaction is reasonably complete. Suitable methods for sulfitating olefins appear in U.S. Pat. Nos. 2,653,970; 4,087,457; 4,275,013, the teachings of which are incorporated herein by reference.

The fatty amines, fatty amidoamines, and their oxidized, reduced, sulfonated, and sulfitated derivatives can be incorporated into many compositions for use as, for example, surfactants, emulsifiers, skin-feel agents, film formers, rheological modifiers, biocides, biocide potentiators, solvents, release agents, and conditioners. The compositions find value in diverse end uses, such as personal care (liquid cleansing products, conditioning bars, oral care products), household products (liquid and powdered laundry detergents, liquid and sheet fabric softeners, hard and soft surface cleaners, sanitizers and disinfectants), and industrial or institutional cleaners.

The fatty amines or amidoamines and their derivatives can be used in emulsion polymerizations, including processes for the manufacture of latex. They can be used as surfactants, wetting agents, dispersants, or solvents in agricultural applications, as inert ingredients in pesticides, or as adjuvants for delivery of pesticides for crop protection, home and garden, and professional applications. The fatty amines or amidoamines and their derivatives can also be used in oil field applications, including oil and gas transport, production, stimulation and drilling chemicals, reservoir conformance and enhancement uses, and specialty foamers. The compositions are also valuable as foam moderators or dispersants for the manufacture of gypsum, cement wall board, concrete additives and firefighting foams. The compositions are useful as coalescents for paints and coatings, and as polyurethane-based adhesives.

In food and beverage processing, the fatty amines or amidoamines and their derivatives can be used to lubricate the conveyor systems used to fill containers. When combined with hydrogen peroxide, the fatty amines or amidoamines and their derivatives can function as low foaming disinfectants and sanitization agents, odor reducers, and as antimicrobial agents for cleaning and protecting food or beverage processing equipment. In industrial, institutional and laundry applications, the fatty amines or amidoamines and their derivatives, or their combination with hydrogen peroxide, can be used to remove soil and sanitize and disinfect fabrics and as antimicrobial film-forming compositions on hard surfaces.

The following examples merely illustrate the invention. Those skilled in the art will recognize many variations that are within the spirit of the invention and scope of the claims.

Feedstock Syntheses

Preparation of Methyl 9-Decenoate ("C10-0") and Methyl 9-Dodecenoate ("C12-0")

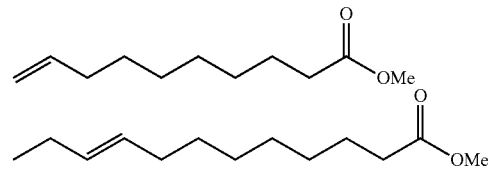

The procedures of U.S. Pat. Appl. Publ. No. 2011/0113679, the teachings of which are incorporated herein by reference, are used to generate feedstocks C10-0 and C12-0 as follows:

Example 1A

Cross-Metathesis of Soybean Oil and 1-Butene

A clean, dry, stainless-steel jacketed 5-gallon Parr reactor equipped with a dip tube, overhead stirrer, internal cooling/heating coils, temperature probe, sampling valve, and relief valve is purged with argon to 15 psig. Soybean oil (SBO, 2.5 kg, 2.9 mol, Costco, $M_n$=864.4 g/mol, 85 weight % unsaturation, sparged with argon in a 5-gal container for 1 h) is added to the Parr reactor. The reactor is sealed, and the SBO is purged with argon for 2 h while cooling to 10° C. After 2 h, the reactor is vented to 10 psig. The dip tube valve is connected to a 1-butene cylinder (Airgas, CP grade, 33 psig headspace pressure, >99 wt. %) and re-pressurized to 15 psig with 1-butene. The reactor is again vented to 10 psig to remove residual argon. The SBO is stirred at 350 rpm and 9-15° C.

under 18-28 psig 1-butene until 3 mol 1-butene per SBO olefin bond are transferred into the reactor (~2.2 kg 1-butene over 4-5 h).

A toluene solution of [1,3-bis-(2,4,6-trimethylphenyl)-2-imidazolidinylidene]-dichlororuthenium(3-methyl-2-butenylidene)(tricyclohexylphosphine) (C827, Materia) is prepared in a Fischer-Porter pressure vessel by dissolving 130 mg catalyst in 30 g of toluene (10 mol ppm per mol olefin bond of SBO). The catalyst mixture is added to the reactor via the reactor dip tube by pressurizing the headspace inside the Fischer-Porter vessel with argon to 50-60 psig. The Fischer-Porter vessel and dip tube are rinsed with additional toluene (30 g). The reaction mixture is stirred for 2.0 h at 60° C. and is then allowed to cool to ambient temperature while the gases in the headspace are vented.

After the pressure is released, the reaction mixture is transferred to a round-bottom flask containing bleaching clay (Pure-Flo® B80 CG clay, product of Oil-Dri Corporation of America, 2% w/w SBO, 58 g) and a magnetic stir bar. The reaction mixture is stirred at 85° C. under argon. After 2 h, during which time any remaining 1-butene is allowed to vent, the reaction mixture cools to 40° C. and is filtered through a glass frit. An aliquot of the product mixture is transesterified with 1% w/w NaOMe in methanol at 60° C. By gas chromatography (GC), it contains: methyl 9-decenoate (22 wt. %), methyl 9-dodecenoate (16 wt. %), dimethyl 9-octadecenedioate (3 wt. %), and methyl 9-octadecenoate (3 wt. %).

The results compare favorably with calculated yields for a hypothetical equilibrium mixture: methyl 9-decenoate (23.4 wt. %), methyl 9-dodecenoate (17.9 wt %), dimethyl 9-octadecenedioate (3.7 wt. %), and methyl 9-octadecenoate (1.8 wt. %).

Example 1B

The procedure of Example 1A is generally followed with 1.73 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (18 wt. %), dimethyl 9-octadecenedioate (2 wt. %), and methyl 9-octadecenoate (2 wt. %).

Example 1C

The procedure of Example 1A is generally followed with 1.75 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (17 wt. %), dimethyl 9-octadecenedioate (3 wt. %), and methyl 9-octadecenoate (2 wt. %).

Example 1D

The procedure of Example 1A is generally followed with 2.2 kg SBO and 3 mol 1-butene/SBO double bond. Additionally, the toluene used to transfer the catalyst (60 g) is replaced with SBO. An aliquot of the product mixture is transesterified with sodium methoxide in methanol as described above. The products (by GC) are: methyl 9-decenoate (25 wt. %), methyl 9-dodecenoate (18 wt. %), dimethyl 9-octadecenedioate (3 wt. %), and methyl 9-octadecenoate (1 wt. %).

Example 1E

Separation of Olefins from Modified Triglyceride

A 12-L round-bottom flask equipped with a magnetic stir bar, heating mantle, and temperature controller is charged with the combined reaction products from Examples 1A-1D (8.42 kg). A cooling condenser with a vacuum inlet is attached to the middle neck of the flask and a receiving flask is connected to the condenser. Volatile hydrocarbons (olefins) are removed from the reaction product by vacuum distillation. Pot temperature: 22° C.-130° C.; distillation head temperature: 19° C.-70° C.; pressure: 2000-160 µtorr. After removing the volatile hydrocarbons, 5.34 kg of non-volatile residue remains. An aliquot of the non-volatile product mixture is transesterified with sodium methoxide in methanol as described above. The products (by GC) are: methyl 9-decenoate (32 wt. %), methyl 9-dodecenoate (23 wt. %), dimethyl 9-octadecenedioate (4 wt. %), and methyl 9-octadecenoate (5 wt. %). This mixture is also called "UTG-0." (An analogous product made from palm oil is called "PUTG-0.")

Example 1F

Methanolysis of Modified Triglyceride

A 12-L round-bottom flask fitted with a magnetic stir bar, condenser, heating mantle, temperature probe, and gas adapter is charged with sodium methoxide in methanol (1% w/w, 4.0 L) and the non-volatile product mixture produced in Example 1E (5.34 kg). The resulting light-yellow heterogeneous mixture is stirred at 60° C. After 1 h, the mixture turns homogeneous and has an orange color (pH=11). After 2 h of reaction, the mixture is cooled to ambient temperature and two layers form. The organic phase is washed with aqueous methanol (50% v/v, 2×3 L), separated, and neutralized by washing with glacial acetic acid in methanol (1 mol HOAc/mol NaOMe) to pH=6.5. Yield: 5.03 kg.

Example 1G

Isolation of Methyl Ester Feedstocks

A 12-L round-bottom flask fitted with a magnetic stirrer, packed column, and temperature controller is charged with the methyl ester mixture produced in example 1F (5.03 kg), and the flask is placed in a heating mantle. The glass column is 2"×36" and contains 0.16" Pro-Pak™ stainless-steel saddles (Cannon Instrument Co.). The column is attached to a fractional distillation head to which a 1-L pre-weighed flask is fitted for collecting fractions. Distillation is performed under vacuum (100-120 µtorr). A reflux ratio of 1:3 is used to isolate methyl 9-decenoate ("C10-0") and methyl 9-dodecenoate ("C12-0"). Samples collected during the distillation, distillation conditions, and the composition of the fractions (by GC) are shown in Table 1. A reflux ratio of 1:3 refers to 1 drop collected for every 3 drops sent back to the distillation column. Combining appropriate fractions yields methyl 9-decenoate (1.46 kg, 99.7% pure) and methyl 9-dodecenoate (0.55 kg, >98% pure).

TABLE 1

Isolation of C10-0 and C12-0 by Distillation

| Distillation Fractions # | Head temp. (° C.) | Pot temp. (° C.) | Vacuum (µtorr) | Weight (g) | C10-0 (wt %) | C12-0 (wt %) |
|---|---|---|---|---|---|---|
| 1 | 40-47 | 104-106 | 110 | 6.8 | 80 | 0 |
| 2 | 45-46 | 106 | 110 | 32.4 | 99 | 0 |
| 3 | 47-48 | 105-110 | 120 | 223.6 | 99 | 0 |
| 4 | 49-50 | 110-112 | 120 | 283 | 99 | 0 |
| 5 | 50 | 106 | 110 | 555 | 99 | 0 |
| 6 | 50 | 108 | 110 | 264 | 99 | 0 |

TABLE 1-continued

Isolation of C10-0 and C12-0 by Distillation

| Distillation Fractions # | Head temp. (° C.) | Pot temp. (° C.) | Vacuum (μtorr) | Weight (g) | C10-0 (wt %) | C12-0 (wt %) |
|---|---|---|---|---|---|---|
| 7 | 50 | 112 | 110 | 171 | 99 | 0 |
| 8 | 51 | 114 | 110 | 76 | 97 | 1 |
| 9 | 65-70 | 126-128 | 110 | 87 | 47 | 23 |
| 10 | 74 | 130-131 | 110 | 64 | 0 | 75 |
| 11 | 75 | 133 | 110 | 52.3 | 0 | 74 |
| 12 | 76 | 135-136 | 110 | 38 | 0 | 79 |
| 13 | 76 | 136-138 | 100 | 52.4 | 0 | 90 |
| 14 | 76 | 138-139 | 100 | 25.5 | 0 | 85 |
| 15 | 76-77 | 140 | 110 | 123 | 0 | 98 |
| 16 | 78 | 140 | 100 | 426 | 0 | 100 |

Precursor Syntheses:
C10-25: C10 DMA Amide

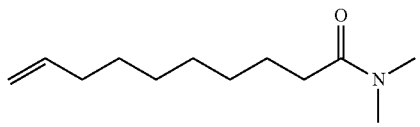

A round-bottom flask is charged with methyl ester feedstock C10-0 (235 g) and the mixture is degassed with nitrogen. Sodium methoxide (5 g of 30% solution in methanol) is added via syringe and the mixture is stirred for 5 min. Dimethylamine (67 g) is slowly added via sub-surface dip tube. After the addition, the mixture is heated to 60° C. and held overnight. The amide, C10-25, is recovered via vacuum distillation (120° C., 20 mm Hg). Yield: 241.2 g (96.3%). Iodine value=128.9 g I$_2$/100 g sample. $^1$H NMR (CDCl$_3$), δ (ppm)= 5.8 (CH$_2$=CH—); 4.9 (CH$_2$=CH—); 2.8-3.0 (—C(O)—N (CH$_3$)$_2$); 2.25 (—CH$_2$—C(O)—). Ester content (by $^1$H NMR): 0.54%.

C12-25: C12 DMA Amide

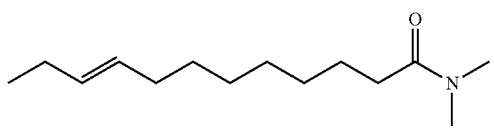 [SMILES: CC/C=C/CCCCCCCC(=O)N(C)C]

A round-bottom flask is charged with methyl ester C12-0 (900 g) and the feedstock is degassed with nitrogen at 60° C. Sodium methoxide (30 g of 30% solution in methanol) is added via syringe and the mixture is stirred for 5 min. Vacuum is then applied and the reaction vessel sealed. Dimethylamine (200 g) is slowly added via sub-surface dip tube against the static vacuum. After the addition, the remaining vacuum is released with nitrogen, and the mixture is heated to 70° C. for 1 h. The mixture is heated to 80° C., DMA is sparged through the liquid for 2 h, and the mixture is then heated to 90° C. for 1 h. The sparge is stopped, and the reaction is cooled to 75° C. Full vacuum is applied and held for 0.5 h. The vacuum is released, and 50% H$_2$SO$_4$ (16.3 g) and deionized water (200 mL) are added to quench the catalyst. The organic layer is washed with deionized water (2×300 mL, then 1×150 mL) and then 20% brine solution (50 mL). The organic layer is concentrated (full vacuum, 75° C.) and vacuum distilled (pot: 140-150° C.) to isolate amide C12-25. Iodine value: 112.8 g I$_2$/100 g sample; % moisture: 65 ppm. $^1$H NMR (CDCl$_3$), δ (ppm): 5.35 (—CH=CH—); 2.8-3.0 (—C(O)—N(CH$_3$)$_2$; 2.25 (—CH$_2$—C(O)—).

Amine Syntheses:
C10-38: C10 Amine

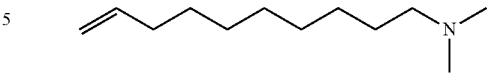

Amide C10-25 (475 g) is slowly added over 3 h to a stirring THF slurry of LiAlH$_4$ (59.4 g) under nitrogen while maintaining the temperature at 11-15° C. The mixture warms to room temperature and stirs overnight. The mixture is chilled in an ice bath, and water (60 g) is added cautiously, followed by 15% aq. NaOH solution (60 g) and then additional water (180 g) is added. The mixture warms to room temperature and is stirred for 1 h. The mixture is filtered, and the filter cake is washed with THF. The filtrates are combined and concentrated. NMR analysis of the crude product indicates that it contains approximately 16% 9-decen-1-ol, a side-product formed during the reduction of the amide. In order to sequester the alcohol, phthalic anhydride is to be added, thus forming the half-ester/acid. The product mixture is heated to 60° C. and phthalic anhydride (57.5 g) is added in portions. NMR analysis of the mixture shows complete consumption of the alcohol, and the mixture is vacuum distilled to isolate C10-38. Amine value: 298.0 mg KOH/g; iodine value: 143.15 g I$_2$/100 g sample; % moisture: 0.02%. $^1$H NMR (CDCl$_3$), δ (ppm): 5.8 (CH$_2$=CH—); 4.9 (CH$_2$=CH—); 3.7 (—CH$_2$—N(CH$_3$)$_2$).

C12-26: C12 Amine

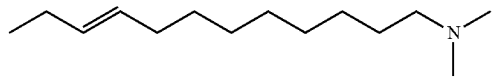

The procedure used to make C10-38 is generally followed with amide C12-25 (620 g) and LiAlH$_4$ (67.8 g). When the reaction is complete, water (68 g) and 15% aq. NaOH solution (68 g) and water (204 g) are used to quench the reaction. After the usual filtration and concentration steps, NMR analysis of the crude product shows approximately 16% 9-dodecen-1-ol to be present. And phthalic anhydride (30 g) is added in order to sequester the alcohol. The mixture is then vacuum distilled to give C12-26. Amine value: 258.1 mg KOH/g sample; iodine value: 120.0 g I$_2$/100 g sample. $^1$H NMR (CDCl$_3$), δ: 5.35 (—CH=CH—); 2.2 (—CH$_2$—N(CH$_3$)$_2$).

Amine Oxides from Amines:
C10-39: C10 Amine Oxide

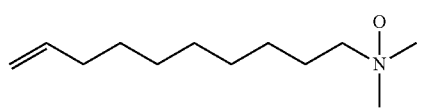

A round-bottom flask is charged with amine C10-38 (136 g), water (223 g), and Hamp-Ex 80 (pentasodium diethylenetriamine pentaacetate solution, 0.4 g). The mixture is heated to 50° C. and dry ice is added until the pH is ~7.0. When the pH stabilizes, hydrogen peroxide (35% solution, 73.5 g) is added dropwise, and the ensuing exotherm is allowed to heat the mixture to 75° C. When the peroxide addition is complete, the mixture is maintained at 75° C. for 18 h. Stirring continues at 75° C. until the residual peroxide level is <0.2%. $^1$H NMR analysis indicates a complete reaction, and the solution is cooled to room temperature to give amine oxide C10-39. Residual peroxide: 0.13%; free tertiary amine: 0.63%; amine oxide: 32.6%.

C12-28: C12 Amine Oxide

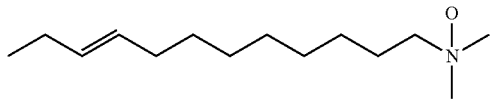

A round-bottom flask equipped with an overhead mechanical stirrer and addition funnel is charged with deionized water (93.5 g) and Hamp-Ex 80 (0.3 g). The mixture is heated to 50° C. while amine C12-26 (137 g, 0.65 mol) and dry ice (~5 g) are added. Hydrogen peroxide (35% solution, 64.3 g, 0.66 mol) is added dropwise to the reaction mixture, allowing the mixture to exotherm to 80° C. and then controlling the reaction at this temperature using a water bath for cooling. The mixture thickens after two-thirds of the $H_2O_2$ has been added, and more deionized water (73.7 g) is added. After completing the peroxide addition, the mixture stirs at 80° C. for 24 h until a peroxide test strip indicates low residual peroxide. The ~40% solids reaction mixture is diluted with water to ~37.5% solids to afford a homogenous solution. Titration shows 37.2% C12 amine oxide and 0.009% free amine. Analysis by $^1$H NMR (CDCl$_3$) confirms the formation of the amine oxide, based on shift of the N(CH$_3$)$_2$ peak from 2.18 ppm (for the amine) to 3.12 ppm.

Amidoamine Syntheses:
C10-17: C10 DMAPA Amide

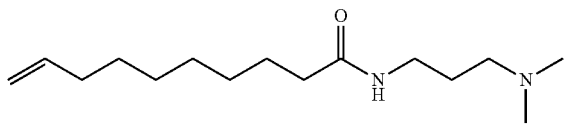 [SMILES: C=CCCCCCCCC(=O)NCCCN(C)C]

A round-bottom flask equipped with nitrogen sparge tube, mechanical stirrer, and Dean-Stark trap is charged with methyl ester C10-0 (500 g, 2.7 mol), 3-(dimethyl-amino) propylamine ("DMAPA," 331 g, 3.24 mol), and sodium methoxide (8.3 g of a 30% solution of in methanol). The reaction mixture is heated to 100° C. and methanol is collected. The reaction temperature is increased in 5° C. increments until the temperature reaches 130° C. The mixture is held at 130° C. for 1 h, and then a sub-surface nitrogen sparge is applied for 2.5 h. The temperature is elevated to 140° C. for an additional 3.5 h. Collected distillate (122 mL) includes methanol and some DMAPA. The reaction mixture is cooled to 110° C., the nitrogen sparge is discontinued, and vacuum was applied. The mixture is stripped of excess DMAPA (150° C., 20 mm Hg, 30 min.). The product, amidoamine C10-17, has an amine value of 224.14 (eq. wt.: 250.28). $^1$H NMR (CDCl$_3$) confirms formation of the amide, based on disappearance of the methyl ester peak at 3.61 ppm and appearance of the DMAPA CH$_2$ signals at 3.27, 2.09, and 1.60 ppm and the N(CH$_3$)$_2$ at 2.18 ppm.

C12-17: C12 DMAPA Amide

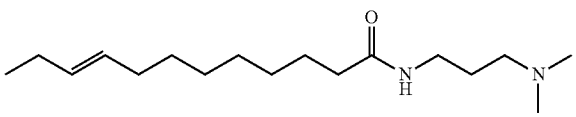 [SMILES: CC/C=C/CCCCCCCC(=O)NCCCN(C)C]

The procedure used to make C10-17 is generally followed with methyl ester C12-0 (670 g), DMAPA (387 g), and sodium methoxide (11.2 g of 30 wt. % solution in methanol). The resulting product, amidoamine C12-17, has an amine value of 196.39 (eq. wt.: 281.3). $^1$H NMR (CDCl$_3$) confirms formation of the amide, based on disappearance of the methyl ester peak at 3.61 ppm and appearance of the DMAPA CH$_2$ signals at 3.30, 2.11, and 1.62 ppm and the N(CH$_3$)$_2$ at 2.20 ppm.

Amine Oxides from Amidoamines:
C10-20: C10 DMAPA AO

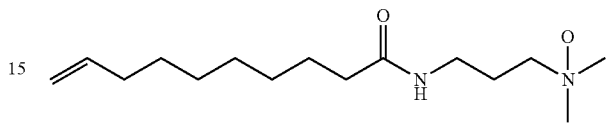

A round-bottom flask is charged with amidoamine C10-17 (162.6 g), water (267 g), and Hamp-Ex 80 (0.5 g). The mixture is heated to 50° C. under nitrogen and several small pieces of dry ice are added. Hydrogen peroxide (35 wt. % aqueous solution, 64.5 g) is added dropwise while keeping the temperature less than 75° C. After completing the $H_2O_2$ addition, the mixture is maintained at 70° C. for 7 h. Peroxide paper test indicates <0.5% residual $H_2O_2$. The mixture is heated for 3 h at 75° C. and then cooled to room temperature to give amine oxide C10-20 in water. The product comprises (by titration): 35.2% amine oxide; 0.85% free amine.

C12-20: C12 DMAPA AO

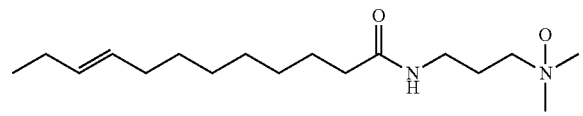

A round-bottom flask is charged with amidoamine C12-17 (250 g), water (400 g), and Hamp-Ex 80 (0.7 g). Dry ice is added until the pH is 8-9. The mixture is heated to 50° C. under nitrogen. Hydrogen peroxide (35 wt. % solution, 88 g) is added dropwise while maintaining the temperature at less than 75° C. The mixture is maintained at 70° C. for 3 h, then cooled to room temperature overnight. The mixture is reheated to 75° C. and water (50 g) is added to help dissolve solids. The mixture is held at 75° C. for 4 h. Analysis with peroxide test strips indicates trace residual peroxide. The mixture is cooled to recover amine oxide C12-20 as an aqueous solution. The product comprises (by titration): 33.4% amine oxide; 0.06% free amine.

Sulfonated Derivatives from Amidoamines:
C10-21: C10 DMAPA AO Sulfonate

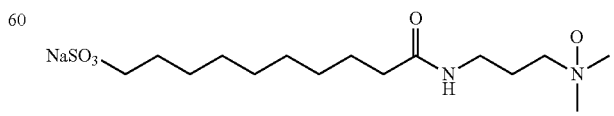

A round-bottom flask equipped with stir bar, condenser, and thermocouple is charged with amine oxide C10-20 (212.4 g, 36.8% solids) and sodium metabisulfite (Na$_2$S$_2$O$_5$; 28.09 g, 1.03 eq. NaHSO$_3$), and this mixture is stirred until homogeneous. The solution is heated to 80° C. and the pH is adjusted to 7.5 with SO$_2$ gas. After 30 min., the pH is adjusted again with SO$_2$ to 7.5. After 1 h, the pH is adjusted a third time with SO$_2$ and is then heated at 80° C. overnight. After 16 h, $^1$H NMR analysis (D$_2$O) indicates a complete reaction. The signal for the amine oxide methyl group had shifted to 2.6 ppm (from 3.1 ppm in the starting material), indicating conversion of amine oxide to sulfitoamine. Sodium hydroxide (5.46 g, 0.2 eq.) is added to hydrolyze the sulfitoamine and the mixture is heated at 80° C. overnight. After 16 h, $^1$H NMR analysis indicates that the amine methyl signal has shifted to 2.2 ppm, indicating hydrolysis of sulfitoamine to the corresponding amine. The mixture is cooled to 50° C. and the pH is adjusted from 10.1 to 8.3 by adding dry ice. Hydrogen peroxide (28.43 g, 1.02 eq.) is added dropwise, maintaining the reaction temperature below 70° C. The mixture is maintained at 70° C. for 16 h. The mixture is cooled to provide sulfonate C10-21 as an aqueous solution. Analysis by $^1$H NMR (D$_2$O) confirms formation of the amine oxide sulfonate, based appearance of the N(CH$_3$)$_2$ at 3.2 ppm, which matches up well with the N(CH$_3$)$_2$ in the starting amine oxide, and a new signal at 2.7 ppm corresponding to the protons adjacent to the sulfonate group (—CH$_2$SO$_3$Na).

C12-42: C12 DMAPA Sulfonate

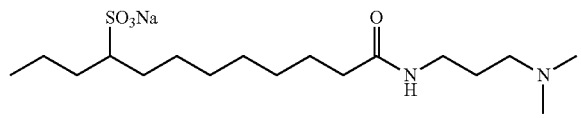

Amidoamine C12-17 (193.7 g) and isopropyl alcohol ("IPA," 400 g) are charged to a flask equipped with a mechanical stirrer and a thermocouple. A solution prepared from sodium metabisulfite (65.5 g), sodium sulfite (8.4 g), and deionized water (400 g) is added. The mixture is heated to 75° C., and the pH is adjusted from 7.5 to 6.5 with SO$_2$ gas. tert-Butylperoxybenzoate (TBB, 1 mL) is added. Over the next 16 h, additional water (200 g), IPA (100 g), and TBB (2.2 mL) are added. The pH is adjusted three additional times with SO$_2$ to 6.5. Upon cooling, the reaction mixture is stripped to remove IPA, and the pH of the liquid product is adjusted to 9.0 by adding NaOH. The aqueous sulfonated product (982 g) is analyzed. $^1$H NMR (D$_2$O) indicates 80% conversion of starting olefin based on integration of residual olefin proton signals at 5.2-5.5 ppm. Formation of the sulfonated product is confirmed by the presence of a new signal at 2.4-2.6 ppm, corresponding to the proton adjacent to the sulfonate. The product comprises, in addition to the sulfonate, 60.1% water, 3.63% IPA, 5.15% Na$_2$SO$_4$, and 1.99% Na$_2$SO$_3$.

C12-21: C12 DMAPA AO Sulfonate

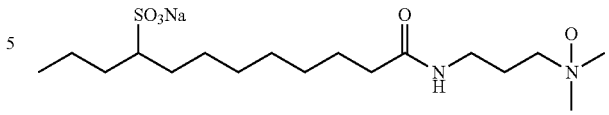

Sulfonate C12-42 (405.5 g) and Hamp-Ex 80 (0.37 g) are charged to a round-bottom flask. The mixture is heated to 50° C. and aqueous hydrogen peroxide (35%, 46.65 g) is added dropwise without additional heating, maintaining the reaction temperature below 75° C. The mixture is maintained at 85° C. for 36 h. Sodium thiosulfate titration indicates that the product contains 0.9% residual hydrogen peroxide. Water content: 63.93%. $^1$H NMR (D$_2$O) indicates 70% conversion of starting tertiary amine to the amine oxide, based on integration of the N(CH$_3$)$_2$ peaks at 2.74 ppm, for the amine, to 3.25 ppm, for the amine oxide.

Preparation of Methyl 9-Hexadecenoate ("C16-0") Feedstock

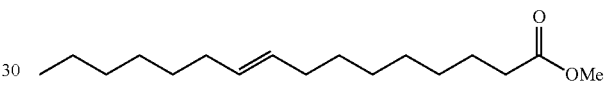

The procedures of Example 1A is generally followed except that 1-octene is cross-metathesized with soybean oil instead of 1-butene. Combined reaction products are then stripped as described in Example 1E to remove the more volatile unsaturated hydrocarbon fraction from the modified oil fraction. The procedure of Example 1F is used to convert the modified oil fraction to a methyl ester mixture that includes methyl 9-hexadecenoate. Fractional distillation at reduced pressure is used to isolate the desired product, methyl 9-hexadecenoate from other methyl esters.

C16-9: C16 DMAPA Amide:

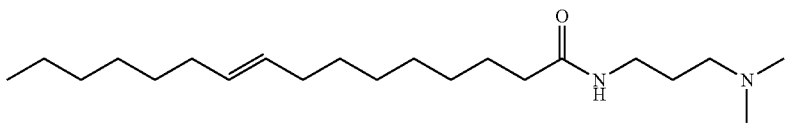 [SMILES: CCCCCC/C=C/CCCCCCCC(=O)NCCCN(C)C]

A round-bottom flask equipped with nitrogen sparge tube, mechanical stirrer, and Dean-Stark trap is charged with methyl ester C16-0 (505.2 g), DMAPA (223.2 g), and sodium methoxide (12.6 g of a 30% solution of in methanol). The reaction mixture is heated to 105° C. and methanol is collected. The reaction temperature is increased gradually until the temperature reaches 140° C. The mixture is held at 140° C. for 2 h. The reaction mixture is cooled to 100° C., and vacuum is applied, with temperature gradually increased to 120° C. Analysis after a weekend at room temperature shows a complete reaction. Residual DMAPA is stripped (130° C., full vacuum, 3 h). The product, amidoamine C16-9, has eq. wt.: 339.5, free DMAPA: 0.56%, and a $^1$H NMR spectrum consistent with the expected structure.

C16-11: C16-DMAPA Sulfonate:

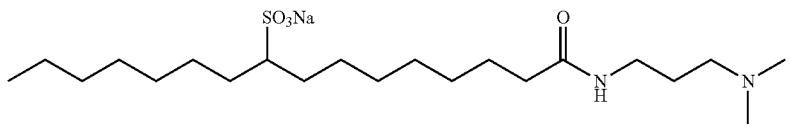

Amide C16-9 (228.4 g) is charged to a round-bottom flask equipped with an agitator, condenser, and thermocouple, and isopropyl alcohol (IPA, 530 g) is added. Sodium sulfite (33.6 g) is dissolved in water and added to the amide solution, followed by tert-butylperoxybenzoate (TBB, 1.3 g). The mixture is heated to 75° C., and the pH is adjusted from 8.2 to 6.9 with $SO_2$. The pH rises over the first 4 h and is adjusted down to 6.9 with $SO_2$. The mixture stirs overnight. The remaining sodium sulfite (33.6 g) is added and no pH adjustment is needed. More TBB (1.3 g) is added and the reaction mixture stirs overnight at 75° C. $^1$H NMR analysis shows 50% conversion. The pH is adjusted from 6.5 to 6.7, more TBB (1.0 mL) is added, and the mixture stirs overnight at 75° C. Conversion reaches 63%, and a significant amount of $SO_2/SO_3$ remains, so the pH is adjusted to 6.8 and stirring continues. Prolonged heating fails to significantly improve conversion, and the reaction is discontinued. IPA and water are stripped to give C16-11 as a solution of 48% solids. Moisture: 52.1%; pH: 6.34; inorganic sulfate: 7.43%; $Na_2SO_3$: 3.45%; conversion of C16-9 to sulfitated amidoamine (by $^1$H NMR): 67.5%.

C16-12: C16 DMAPA Sulfonate AO

A round-bottom flask is charged with DMAPA sulfonate C16-11 (442.3 g), water (490 g), and Hamp-Ex 80 (1.3 g). Hydrogen peroxide (35% solution, 106 g) is added dropwise, keeping the temperature below 75° C. by external cooling as needed. At the end of the addition, the mixture is held at 75° C. for 18 h. Analysis of the mixture by thiosulfate titration shows a high level of residual peroxide, and stirring continues at 75° C. until the level is <1%. The solution is cooled to room temperature and the amine oxide product, C16-12, is analyzed. The $^1$H NMR spectrum is consistent with the target structure and shows no residual free amine.

Feedstock Synthesis

Preparation of Dimethyl 9-Octadecene-1,18-dioate ("Mix-0" or "C18-0")

Eight samples of methyl 9-dodecenoate (10.6 g each, see Table 2) are warmed to 50° C. and degassed with argon for 30 min. A metathesis catalyst ([1,3-bis-(2,4,6-trimethylphenyl)-2-imidazolidinylidene]dichlororuthenium(3-methyl-2-butenylidene)-(tricyclohexylphosphine), product of Materia) is added to the methyl 9-dodecenoate (amount indicated in Table 2) and vacuum is applied to provide a pressure of <1 mm Hg. The reaction mixture is allowed to self-metathesize for the time reported. Analysis by gas chromatography indicates that dimethyl 9-octadecene-1,18-dioate is produced in the yields reported in Table 2. "Mix-0" is an 80:20 trans-/cis-isomer mixture obtained from the reaction mixture. Crystallization provides the all-trans-isomer feed, "C18-0."

TABLE 2

Self-Metathesis of Methyl 9-Dodecanoate

| Sample | Catalyst Loading (ppm mol/mol)* | Reaction Time (h) | C18-0 (GC Area %) |
|---|---|---|---|
| A | 100 | 3 | 83.5 |
| B | 50 | 3 | 82.5 |
| C | 25 | 3 | 83.0 |
| D | 10 | 3 | 66.2 |
| E | 15 | 4 | 90.0 |
| F | 13 | 4 | 89.9 |
| G | 10 | 4 | 81.1 |
| H | 5 | 4 | 50.9 |

*ppm mol catalyst/mol methyl 9-dodecenoate

C18 Dibasic Acid Derivatives:
C18-26: C18 DiDMAPA Amide (100% trans-)

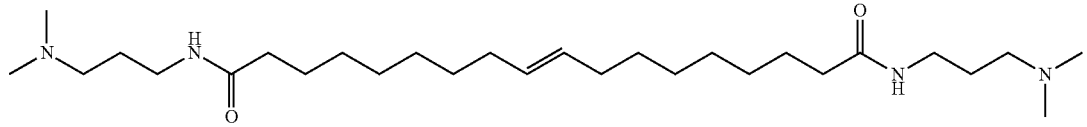

A round-bottom flask equipped with a mechanical stirrer is charged with diester C18-0 (545.6 g) and DMAPA (343.3 g). A Dean-Stark trap is attached, and sodium methoxide (20 g of 30 wt % solution in MeOH) is added. The temperature is raised to 110° C. over 1.5 h, and methanol is collected. The temperature is increased to 150° C. in increments as the distillation slows. The mixture is held at 150° C. for 6.5 hours and then cooled to room temperature. $^1$H NMR analysis indicates a minor amount of unreacted methyl ester. The mixture is heated to 180° C. for several hours and additional DMAPA

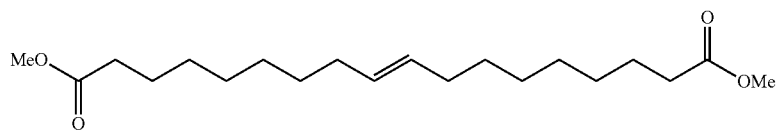 [SMILES: COC(=O)CCCCCCC/C=C/CCCCCCCC(=O)OC]

and sodium methoxide are added. The mixture is cooled and neutralized with concentrated hydrochloric acid. When the mixture has cooled to 90° C., deionized water is added slowly with vigorous agitation, resulting in precipitation of the amide to afford a slurry. Solids are isolated by vacuum filtration and washed with water. The solid product, all-trans amide C18-26, is dried under vacuum. Yield: 92.2%. $^1$H NMR (CDCl$_3$) confirms formation of the amide, based on disappearance of the methyl ester peak at 3.65 ppm and appearance of the DMAPA CH$_2$ signals at 3.31, 2.12, and 1.62 ppm and the N(CH$_3$)$_2$ at 2.20 ppm.

Mix-26: C18 DiDMAPA Amide (80:20 Trans-/Cis-)

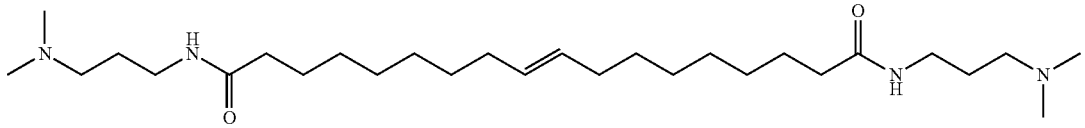

The procedure used to make C18-26 is generally followed with diester Mix-0 (824.3 g), DMAPA (519.5 g), and sodium methoxide (20 g of 30 wt % solution in MeOH). The temperature is increased to 140° C. and held for several hours with a slow nitrogen sparge to assist in removing volatiles. $^1$H NMR analysis shows only a trace of starting ester. The mixture is cooled to 100° C. and dried under full vacuum. The mixture is then neutralized with sulfuric acid (50%, 11 g) and deionized water is added, resulting in precipitation of amide product. The product is vacuum filtered and washed with water. The filtrate is extracted with a mixture of chloroform and ethyl acetate. The organic solvent is evaporated to afford a yellow oil that solidifies upon standing. The oily solids and solids obtained by filtration are combined and dissolved in chloroform. The chloroform is evaporated under reduced pressure and the resulting solid is dried under high vacuum. The product, Mix-26, has an amine value of 229.14 (eq. wt.: 489.7). $^1$H NMR (CDCl$_3$) confirms formation of the amide, based on disappearance of the methyl ester peak at 3.61 ppm and appearance of the DMAPA CH$_2$ signals at 3.31, 2.12, and 1.63 ppm and the N(CH$_3$)$_2$ at 2.21 ppm.

C18-29: C18 DiDMAPA DiAO (100% Trans-)

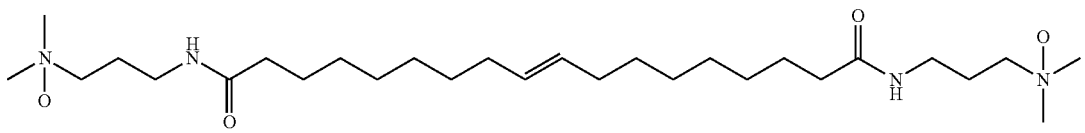

A round-bottom flask is charged with amine C18-26 (141.0 g), water (231.2 g), and Hamp-Ex 80 (0.4 g). The mixture is heated to 50° C. and dry ice is added to pH 8.8. When the pH stabilizes, aqueous H$_2$O$_2$ (35%, 57.8 g) is added dropwise without heating, keeping the temperature below 75° C. After the peroxide addition is complete, the mixture is warmed at 85° C. for 18 h. The mixture is cooled to room temperature. Titrations reveal: amine oxide: 1.32 meq/g; free amine: 0.027 meq/g; free peroxide: 0.0019%; water: 66.4%.

Mix-29: C18 DiDMAPA DiAO (80:20 Trans-/Cis-)

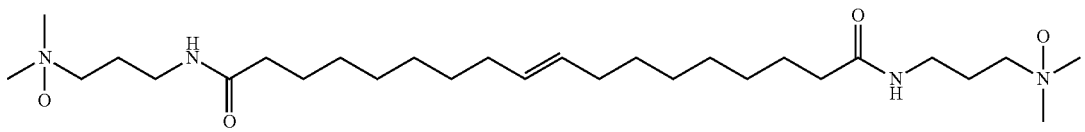

The procedure used to make C18-29 is generally followed with amine Mix-26 (140.0 g), water (230 g), Hamp-Ex 80 (0.4 g), and 35% hydrogen peroxide (57.2 g). Thereafter, titrations indicate: amine oxide: 1.33 meq/g; free amine: 0.046 meq/g; free peroxide: 0.10%; and water: 64.24%.

C18-30: C18 DiDMAPA DiAO Sulfonate

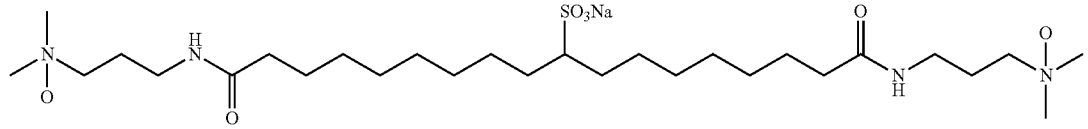

Unsaturated diamide C18-26 (115.38 g) is heated to 60° C. with isopropyl alcohol (700 g) in a round-bottom flask to dissolve the starting material, and t-butylperoxybenzoate (1.25 mL) is added. A solution made from sodium metabisulfite (12.99 g), sodium sulfite (1.67 g), and deionized water (500 g) is added dropwise over 15 min. to the olefin solution. The reaction mixture is stirred at 75° C., the pH is adjusted from 9.0 to 6.5 with $SO_2$, and the mixture is maintained at 75° C. for 16 h. $^1$H NMR analysis shows 54% conversion. The pH is adjusted with $SO_2$ to 6.5 three more times over the next 8 h, and the mixture is then stirred at 75° C. for 16 h. After stripping away solvent, the $^1$H NMR shows negligible residual IPA, and integration of the olefin peaks indicates that the mixture is 77% sulfitated product and 23% starting olefin.

The mixture is transferred to a round-bottom flask. Hamp-Ex 80 (0.32 g) is added, and the resulting solution is heated to 50° C. Aqueous $H_2O_2$ (35%, 47.3 g) is added dropwise without heating, keeping the temperature below 75° C. After the peroxide addition is complete, the mixture is warmed at 85° C. for 18 h. The product is cooled to room temperature and analyzed. Titrations show: free peroxide: 0.25%; water: 63.71%. $^1$H NMR ($D_2O$) indicates complete conversion of the starting diDMAPA amide to the expected amine oxide product as evidenced by disappearance of the $N(CH_3)_2$ peak at 2.20 ppm for the amine and appearance of a peak at 2.73 ppm for the amine oxide $N(CH_3)_2$.

Mix-69: C18 Ester/Acid (80:20 Trans-/Cis-)

portions to the stirred slurry, resulting in dissolution of the solid and formation of a clear solution. The solution is washed three times with water, and the aqueous layers are removed and collected in a separate vessel. The combined aqueous layers are extracted once with ethyl acetate, and the organic phase is combined with the washed product solution. The mixture is dried ($Na_2SO_4$), filtered, and concentrated via rotary evaporator. Thorough drying under high vacuum gives a waxy, crystalline solid upon cooling (655 g, ~70% yield). Analysis of the product (following derivatization) by gas chromatography shows that it contains 94% acid/ester and 6% diacid. Quantitative $^{13}$C NMR shows an 86:14 trans:cis isomer ratio.

Mix-43: C18 Ester/DMAPA Amide (80:20 Trans-/Cis-)

The mixed acid/ester Mix-69 is converted to the acid chloride/ester by reaction with a slight excess of thionyl chloride ($SOCl_2$) in methylene chloride solution and the product is isolated by removal of the solvent and excess $SOCl_2$ under reduced pressure. $^1$H NMR analysis of the isolated product shows essentially quantitative conversion to the acid chloride/ester, and the material is used without further purification.

A 3-L reaction vessel equipped with mechanical stirrer, nitrogen inlet, and thermocouple is charged with methylene chloride (200 mL), DMAPA (172.1 g), and pyridine (133.3 g). The previously prepared acid chloride/ester is added dropwise to the stirred DMAPA-pyridine solution. During the addition, the temperature is maintained at 25-40° C. by cooling with an ice bath as required, and the addition is completed in 1.5 h. A precipitate forms, and after stirring overnight at room temperature, the mixture has become a thick slurry. The mixture is diluted with methylene chloride (500 mL), and water (500 mL) is added, giving a clear homogeneous solution. Addition of ethyl acetate fails to induce phase separation. However, addition of saturated NaCl solution causes

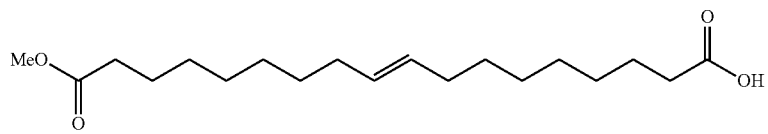 [SMILES: COC(=O)CCCCCCC/C=C/CCCCCCCC(=O)O]

The half-acid/ester Mix-69 is prepared from the dibasic ester Mix-0 (used as received) as described in *Organic Syntheses: Col. Vol. IV* (1963) 635. Thus, Mix-0 (1 kg) is added to methanol (~9 L) and the mixture is stirred mechanically. In a separate vessel, $Ba(OH)_2$ (274.4 g) is dissolved in methanol (~4 L), and the solution is added in portions over 2 h to the stirred diester solution, resulting in the formation of a white precipitate. The solid is isolated by filtration, washed several times with methanol, and dried in air. The solid is then transferred to a 12-L reaction vessel and slurried in ethyl acetate (~3.5 L). Aqueous HCl (32%, Aldrich, 1248.6 g), is added in slow separation of a lower aqueous phase, which is drained and discarded. Concentration of the organic phase via rotary evaporation gives a viscous brown oil. $^1$H NMR analysis shows free pyridine and indicates that the terminal tertiary amine of the DMAPA moiety is protonated. The material is taken up in acetone and the mixture is filtered to remove a small quantity of precipitated solid. The pH of the solution is adjusted to ~8.5 (measured on as-is material) with 50% aq. NaOH, resulting in the formation of a solid precipitate. The mixture is filtered again and the clear filtrate is concentrated and then dried under high vacuum. On cooling, the material solidifies. ¹H NMR analysis is consistent with the target structure and shows the presence of free pyridine. The product is heated to 60° C., stirred, and sparged with sub-surface nitrogen under reduced pressure for 5 h, then at 105° C. for 30 min. After stripping, ¹H NMR analysis of the product showed no residual pyridine.

Mix-46: C18 Ester DMAPA AO (80:20 Trans-/Cis-)

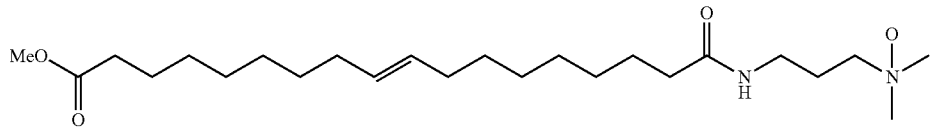

A round-bottom flask fitted with a thermocouple and overhead stirrer is charged with ester-amide Mix-43 (140 g) that has been melted at 50° C., water (240 g), and Hamp-Ex 80 (0.50 g). The mixture is warmed to 50° C. and hydrogen peroxide (33.82 g of 35% aq. solution) is added dropwise. During the addition, the mixture exotherms, and temperature is kept below 75° C. The mixture is stirred at 70° C. for 4 h. Additional hydrogen peroxide solution (1.0 g) is added, and the mixture stirs at 70° C. for an additional 2 h. The product gives a satisfactory ¹H NMR spectrum, free amine, and residual peroxide results. The pH is increased from 6.8 to >8 by adding 50% aq. NaOH (3 g). Analysis shows: moisture: 64.2%; free tertiary amine: 0.15%; amine oxide: 27.5%; residual peroxide: 0.36%.

C18-68: C18 diDMAPA Amide Sulfonate (100% Trans-)

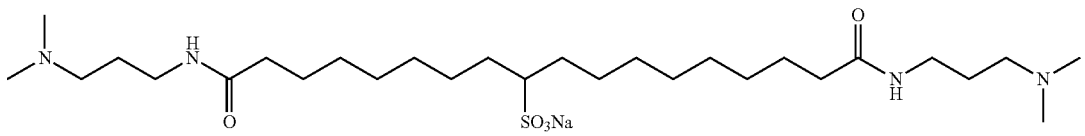

DiDMAPA amidoamine C18-26 (82.9 g) is added to isopropyl alcohol (IPA, 500 g), and the mixture is heated to 60° C. and stirred, giving a homogeneous solution. Sodium sulfite (9.3 g) is dissolved in water (250 g), and the solution is added to the amidoamine solution. The pH is adjusted from 9.2 to 6.5 with gaseous $SO_2$ and t-butylperoxybenzoate (TBB, 0.90 mL) is added. The mixture is stirred at 75° C., and more IPA (50 g) is added to help solubility. Eventually, the mixture thickens and more IPA (50 g) and water (50 g) are added. The mixture stirs overnight. Water (75 g) and more TBB (0.25 mL) are added to the cloudy mixture. Analysis by ¹H NMR after several hours indicates 50% conversion. The mixture stirs overnight, and further analysis shows 59% conversion. A slow $O_2$ sparge is introduced to drive off IPA and the temperature is raised to 80° C. After approximately 6 h, heating is discontinued and the mixture stirs at room temperature over the weekend. Analysis shows 97% conversion. Residual IPA is stripped to give the sulfonate, C18-68. Moisture: 62.6%; inorganic sulfate: 7.28%.

Mix-70: C18 Na Carboxylate/DMAPA Amide (80:20 Trans-/Cis-)

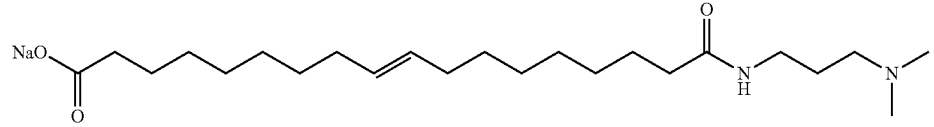

The methyl ester/DMAPA amide Mix-43 (276.8 g) and methanol (500 mL) are charged to a flask equipped with thermocouple, mechanical stirrer, and reflux condenser. The mixture is stirred and heated to 70° C. During heat-up, dropwise addition of NaOH (50% aq. solution, 64.4 g) commences, causing the mixture to thicken to a pasty consistency. When 70° C. is reached and the addition completed, the mixture has become a pasty suspension. The mixture is heated to reflux under nitrogen and held for 3 h. A small aliquot is removed, the volatiles removed under reduced pressure, and the resulting solid analyzed by $^1$H NMR, which reveals complete consumption of the starting methyl ester. The mixture is cooled, stripped via rotary evaporator, and dried under high vacuum overnight. $^1$H NMR analysis shows residual MeOH, and the product is taken up in water (900 g) and subjected to rotary evaporation until $^1$H NMR analysis shows no remaining MeOH. The NMR spectrum is consistent with the target structure. Analysis shows: pH (as-is): 12.8; amine value: 72.3 meq/g; moisture: 72.6%.

Mix-73: C18 Carboxylate DMAPA AO (80:20 Trans-/Cis-)

An aqueous solution of carboxylate-DMAPA amide Mix-70 (758.2 g of a 24% actives solution) is charged to a flask equipped with mechanical stirrer, thermocouple, reflux condenser, and nitrogen inlet. The mixture is warmed to 60° C. and hydrogen peroxide (35% aq. solution, 50.7 g) is added dropwise. The mixture foams up into the condenser, so peroxide addition and agitation are discontinued. The mixture is transferred to 3-L flask and heated to 60° C. The peroxide addition is completed, resulting in a significant lightening of the color. Additional hydrogen peroxide solution (11.6 g) is added, and the mixture is stirred 30 min., then cooled to room temperature overnight. NMR analysis shows incomplete conversion. The mixture is reheated to 60° C. and more hydrogen peroxide is added in portions until conversion is satisfactory. Analysis of the amine oxide, Mix-73, shows: moisture: 79.4%; residual peroxide: 0.03%.

Modified Triglyceride Based on Soybean Oil ("MTG-0")

The procedures of Examples 1A and 1E are generally followed except that 1-butene is omitted.

Mod. Triglyceride from Cross-Metathesis of Soybean Oil and 1-Butene ("UTG-0")

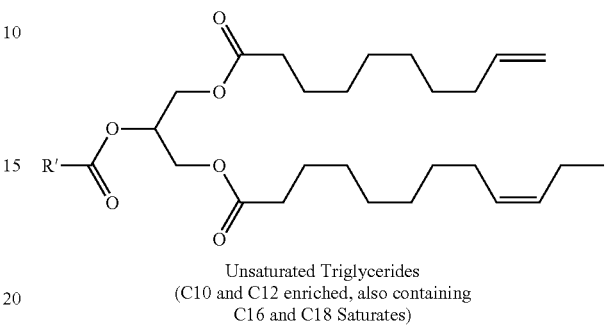

Unsaturated Triglycerides
(C10 and C12 enriched, also containing C16 and C18 Saturates)

The procedures of Examples 1A and 1E are generally followed to produce UTG-0 from soybean oil and 1-butene.

Modified Triglyceride Based on Palm Oil ("PMTG-0")

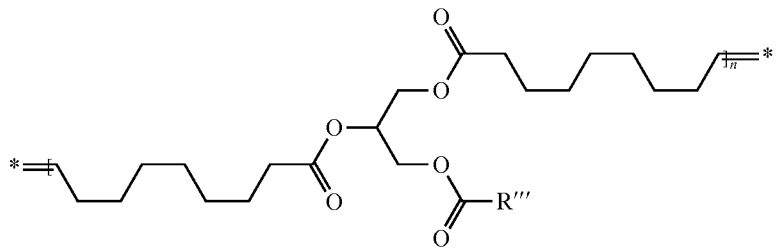

The procedure used to make MTG-0 is followed, except that palm oil is used instead of soybean oil.

Mod. Triglyceride from Cross-Metathesis of Palm Oil and 1-Butene ("PUTG-0")

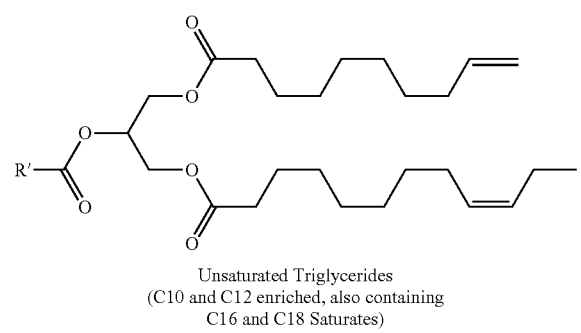

Unsaturated Triglycerides
(C10 and C12 enriched, also containing
C16 and C18 Saturates)

The procedure used to make UTG-0 is followed, except that palm oil is used instead of soybean oil.

MTG-0 Feedstock Derivatives

TABLE 3

Summary of Modified Triglyceride Products

|  | Soybean Oil | | Palm Oil | |
| --- | --- | --- | --- | --- |
|  | Self-met. MTG-0 | X-met. UTG-0 | Self-met. PMTG-0 | X-met. PUTG-0 |
| DMAPA Amide Mix | MTG-5 | UTG-5 | PMTG-5 | PUTG-5 |
| DMAPA AO | MTG-12 | UTG-12 | PMTG-12 | PUTG-12 |

DMAPA = N,N-dimethyl-1,3-propanediamine.

Detailed procedures appear below for preparation of the MTG and PUTG products starting from MTG-0 or PUTG-0. The PMTG products have analogous structures to the MTG products. The UTG products have structures analogous to the PUTG products.

MTG-5: MTG DMAPA Amide Mix

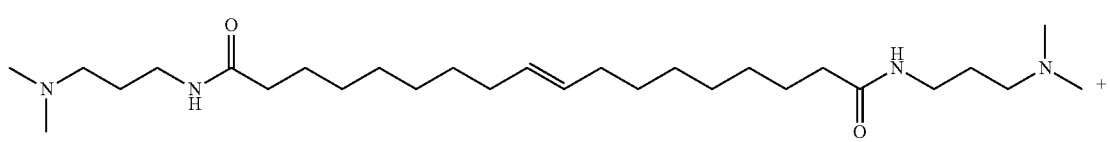

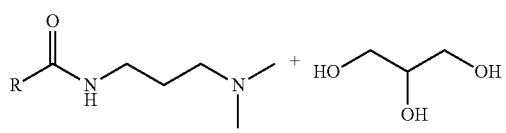

R = C16, C18 Sat. + Unsat.

A round-bottom flask is charged with MTG-0 (180 g, saponification value=226.5 mg KOH/g, 0.73 mol), and the contents are heated to 50° C. The mixture is purged with nitrogen for 1 h and dimethylaminopropylamine (DMAPA, 78 g, 0.76 mol) and NaBH$_4$ (0.1 g) are added. The mixture is heated to 160° C. for 18 h. Excess amine is removed by short-path distillation (135° C., 30 mm Hg), and the product is cooled to room temperature to afford amidoamine mixture MTG-5. Amine value: 172.9 mg KOH/g (eq. wt.: 324.45 g/mol). Free DMAPA: 1.80%; iodine value: 71.9 g I$_2$/100 g sample.

MTG-12: MTG DMAPA AO take-off, and mechanical agitator. The mixture is stirred at 60° C. under nitrogen. Sodium borohydride (0.4 g) is added, and the mixture is stirred for 0.5 h. The mixture is degassed under full vacuum (0.5 h). The vacuum is released with nitrogen and dimethylaminopropylamine (DMAPA, 325 g, 3.18 mol) is then added. The temperature is increased until a gentle reflux of DMAPA occurs (~150° C.). The mixture is held at 150° C. until reflux slows. The temperature is then increased to 160° C. Stirring continues for 4 h at 160° C., and then the mixture is stirred overnight at 150° C. The mixture is cooled to 100° C. and excess DMAPA is removed using a gentle vacuum and dry-ice trap. Vacuum is slowly improved until full vacuum is

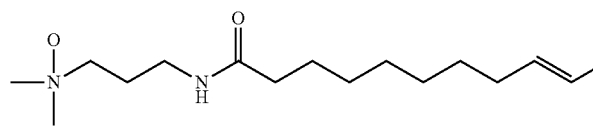

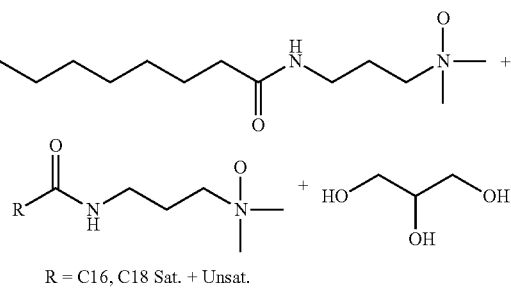

R = C16, C18 Sat. + Unsat.

Molten MTG-5 (145.5 g, 0.42 mol) and deionized water (303.7 g) are charged to a reaction flask equipped with reflux condenser, addition funnel, thermocouple, mechanical stirrer, and nitrogen inlet. The reactor contents are heated to 40° C. with stirring. Dry ice is added in small pieces resulting in a homogeneous solution. Thereafter, 35% H$_2$O$_2$ (43.4 g, 0.47 mol) is added over 15 min., and the reaction temperature increases to 69° C. The initially viscous solution becomes thinner as more peroxide is added. When peroxide addition is complete, the mixture is cooled to 65° C. and allowed to stir for 4 h. Free peroxide: <2 mg/L. The reaction mixture cools to room temperature and stands overnight under a nitrogen purge. The product mixture shows no measurable peroxide. Additional 35% H$_2$O$_2$ solution (2.15 g) is added, and the mixture is heated to 65° C. for 4 h. Upon cooling, analysis of the MTG-12 product shows: pH (10% aqueous): 7.44; water: 69.5%; free amine: 1.52%; amine oxide actives: 29.1%; hydrogen peroxide: 0.01%.

PUTG-5: PUTG DMAPA Amide Mix

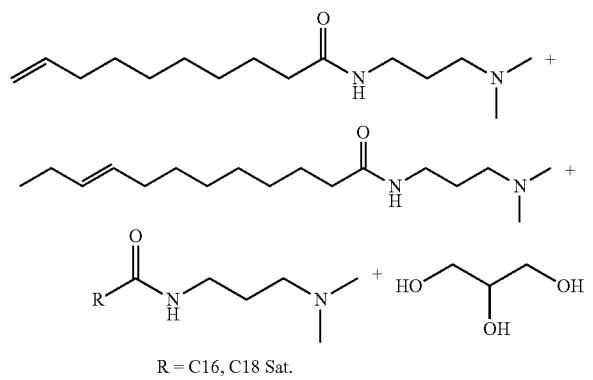

R = C16, C18 Sat.

Molten PUTG-0 (750 g, saponification value: 227.6 mg KOH/g, 3.04 mol) is charged to a reaction vessel equipped with a reflux condenser, thermocouple, nitrogen/vacuum reached. Stripping continues for 1 h. The waxy product, PUTG-5, is titrated with HCl. Acid value: 160.6 meq/g; eq. wt.: 349.4 g/mol. Amine value: 160.56 mg KOH/g; % free DMAPA: 0.08%. $^1$H NMR (CDCl$_3$), δ: 5.8 (CH$_2$=CH—); 5.4 (—CH=CH—); 4.9 (CH$_2$=CH—); 3.2 (—C(O)—NH—CH$_2$—); 2.15 (—N(CH$_3$)$_2$)

PUTG-12: PUTG DMAPA AO

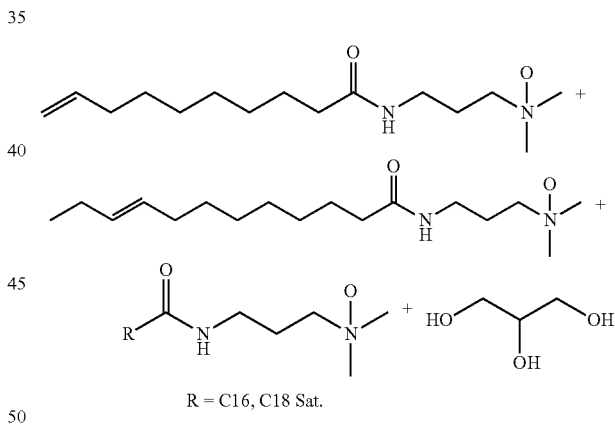

R = C16, C18 Sat.

Molten PUTG-5 (191.2 g; 0.55 mol) is charged to a reaction vessel, and water (325 g) and Hamp-Ex 80 (0.5 g) are then added. The mixture is stirred mechanically, warmed to 50° C., and the headspace is flushed with nitrogen for 0.5 h. Several pieces of dry ice are added, and the mixture stirs for 15 min. Hydrogen peroxide solution (54.3 g of 35% solution, 0.56 mol) is then added dropwise. The ensuing exotherm begins quickly and is allowed to heat the mixture to 70° C. When the addition of H$_2$O$_2$ is complete, the mixture is held at 70° C. for 4 h and then cooled to room temperature overnight. The mixture is reheated to 40° C., and the reaction is judged complete based on a residual peroxide test. $^1$H NMR spectrum of dried material is consistent with the target structure. The liquid product, PUTG-12, is then analyzed to give: pH (10% aqueous): 7.72; amine oxide actives: 35.6%; free amine: 1.09%; peroxide: 0.12%.

Agricultural Glyphosates: Formulation Stability
Sample Preparation:

A 44.0% acid equivalent (a.e.) formulation is prepared by first charging glyphosate acid (486.2 g, 90.5% a.e., product of Monsanto) to an ice-cooled 1-L reaction vessel equipped with a mixer and temperature probe. Deionized water (337.2 g) is added with mixing to generate a glyphosate acid slurry. Potassium hydroxide pellets (176.6 g, 86.6% KOH, Fisher) are slowly added such that the temperature of the solution does not exceed 50° C. The mixture is then allowed to cool to room temperature and is mixed until a clear glyphosate concentrate of 44% a.e. results.

Stability Testing:

A test surfactant (5.0 g) is added to 45.0 g of the glyphosate concentrate above (44% a.e.) to yield a glyphosate formulation concentrate, ~39.6% a.e. (~540 g/L a.e. K salt). This concentrate is mixed until a clear solution results. If no clear solution results, an aliquot of lauryl dimethyl amine oxide (LDMAO, ~50-60% actives, product of Stepan) is added to the surfactant to make a 90:10 surfactant:LDMAO blend. This is then tested for stability as above. If that does not pass, the procedure of adding LDMAO to the surfactant continues until a ratio is found that gives a stable glyphosate formulation. If no stable formulation can be made, the surfactant is deemed incompatible with glyphosate. If a clear homogeneous solution results, the sample is split in two and placed both in a 54° C. oven and a −10° C. freezer for two weeks. If there is no haziness or separation, the formulation is considered stable at that temperature.

The control surfactant is a $C_{12}$-$C_{14}$ DMEA esterquat. This is prepared by reacting a mixture of lauric ($C_{12}$) and myristic ($C_{14}$) acids with N,N-dimethylethanolamine (DMEA) at 140° C. for 5 h, then heating to 175° C. to complete the reaction. Quaternization with methyl chloride in propylene glycol at 80° C. at 40 psig in the usual way provides the desired esterquat. The control surfactant gives a clear formulation at room temperature but the formulation separates at −10 C. Addition of amine oxide in a 9:1 to 1:1 ratio (control surfactant to amine oxide) is needed to give a desirable stability with the control.

As shown in Table 4, eight samples provided superior performance and seven performed as well as similar compounds in the stability testing.

Water-Soluble Herbicide Formulation Testing

Surfactant candidates for water soluble herbicide applications are examined as a replacement for the anionic, nonionic, or anionic/nonionic blend portion and compared to a known industry adjuvant standard for use in paraquat, a water soluble herbicide concentrate formulation. A standard dilution test is conducted whereby the concentrates are diluted in water to determine if solubility is complete.

Control:

Paraquat (9.13 g of 43.8% active material) is added to a 20-mL glass vial. A known industry paraquat adjuvant (2.8 g) is added and vigorously mixed for 30 s. Deionized water (8.07 g) is added, and mixing resumes for 30 s. Standard 342 ppm water (47.5 mL) is added to a 50-mL Nessler cylinder, which is stoppered and equilibrated in a 30° C. water bath. Once the test water equilibrates, the formulated paraquat (2.5 mL) is added by pipette into the cylinder. The cylinder is stoppered and inverted ten times. Solubility is recorded as complete or incomplete. Cylinders are allowed to stand and the amount (in mL) and type of separation are recorded after 30 min., 1 h, 2 h, and 24 h. Results of the solubility testing appear in Table 5 below.

Anionic Test Sample:

Paraquat (4.57 g of 43.8% active material) is added to a 20-mL glass vial. An eight to ten mole alkyl phenol ethoxylate surfactant (0.7 g) is added and vigorously mixed for 30 s. Test sample (0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Nonionic Test Sample:

Paraquat (4.57 g of 43.8% active material) is added to a 20-mL glass vial. Test sample (0.7 g) is added and vigorously mixed for 30 s. Sodium linear alkylbenzene sulfonate ("NaLAS," 0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Adjuvant (Anionic/Nonionic) Test Sample:

Paraquat (4.57 g of 43.8% active material) is added to a 20-mL glass vial. Test sample (1.4 g) is added and vigorously mixed for 30 s. Deionized water (4.03 g) is added, and mixing resumes for 30 s. A 2.5-mL sample of the formulated paraquat

TABLE 4

Glyphosate Formulation Stability: 540 g.a.e./L K salts

| Sample | AO added | Stable at: RT | −10° C. | 54° C. | Comment | Rating |
|---|---|---|---|---|---|---|
| C10-17 | N | Y | Y | Y | low viscosity at −10° C. | superior |
| C10-20 | N | Y | Y | Y |  | superior |
| C12-20 | N | Y | Y | Y | low viscosity at −10° C. | superior |
| C18-26 | N | Y | Y | Y | good results at 5% sample | superior |
| Mix-29 | N | Y | Y | Y |  | superior |
| MTG-5 | N | Y | Y | Y |  | superior |
| PMTG-5 | N | Y | Y | Y |  | superior |
| UTG-12 | N | Y | Y | Y |  | superior |
| C10-39 | N | Y | Y | Y | comparable to decylamine oxide | good |
| C12-17 | Y | Y | Y | Y | 5% sample; +AO for low viscosity | good |
| C12-28 | N | Y | Y | Y |  | good |
| C16-9 | Y | Y | Y | Y | 5% sample; +AO for low viscosity | good |
| Mix-26 | Y | Y | Y | Y |  | good |
| C18-29 | N | Y | Y | Y |  | good |
| PMTG-12 | N | Y | Y | Y | 5% sample; +water for low viscosity | good | is added to 47.5 mL of 342 ppm hardness water, and testing continues as described above for the control sample.

Criteria for emulsion solubility: Test samples should be as good as or better than the control with no separation after one hour. Fifteen test samples perform as well as or better than the control in the emulsion stability test. Results appear in Table 5.

TABLE 5

Water Soluble Herbicide Formulation:
Emulsion stability, mL separation

| test sample | Anionic | | | Nonionic | | | Adjuvant | | | Rating |
|---|---|---|---|---|---|---|---|---|---|---|
| | sol | 1 h | 24 h | sol | 1 h | 24 h | sol | 1 h | 24 h | |
| C10-20 | S | 0 | 0 | D | 1 | 1 | S | 0 | 0 | good |
| C10-21 | S | 0 | 0 | D | 0.25 | 0.5 | S | 0 | 0 | good |
| C10-39 | S | 0 | 0 | I | Floc | Floc | S | 0 | 0 | good |
| C12-20 | S | 0 | 0 | D | 0 | Tr | S | 0 | 0 | good |
| C12-21 | S | 0 | 0 | — | — | — | S | 0 | 0 | good |
| C12-28 | S | 0 | 0 | I | Floc | Floc | S | 0 | 0 | good |
| C16-12 | S | 0 | 0 | D | 0.4 | 0.5 | S | 0 | 0 | good |
| Mix-26 | S | 0 | 0 | I | — | — | I | — | — | good |
| Mix-29 | S | 0 | 0 | D | 0 | Tr | S | 0 | 0 | good |
| C18-30 | S | 0 | 0 | D | Tr | Tr | S | 0 | 0 | good |
| Mix-38 | S | 0 | 0 | D | 0 | 0.25 | S | 0 | 0 | good |
| C18-68 | S | 0 | 0 | D | Tr | Tr | S | 0 | 0 | good |
| MTG-12 | S | 0 | 0 | S | 0 | 0 | S | 0 | 0 | good |
| PMTG-12 | S | 0 | 0 | D | 0 | 0 | S | 0 | 0 | good |
| UTG-12 | S | 0 | 0 | D | 0 | Tr | S | 0 | 0 | good |

D = dispersable;
S = soluble;
I = insoluble;
Tr = trace;
Floc = flocculation observed
Control result: Solubility: D; 1 h: 0 mL; 24 h: Tr.

Acrichemical Solvent Analysis: Active Solubility

Solvency strength of potential agrichemical solvents is evaluated by identifying the solubility level of four standard pesticides in the solvent by weight percent: 2,4-D acid, imidacloprid, trifluralin and tebuconazole. Testing is performed using a 4-mL vial with a pane magnetic stirrer and an accurately weighed 2 to 2.2-g sample of solvent. The active material is also accurately weighed before addition. Initial amounts of active material are approximately: 2,4-D: 0.3 g; imidacloprid: 0.02 g; trifluralin: 0.5 g; tebuconazole: 0.3 g. Solvent and pesticide active are combined, allowed to mix for 1 h at room temperature, and then inspected for the presence of undissolved active material. Additional active material is added in appropriately small increments until it no longer dissolves completely. This mixture is then stirred for 24 h at room temperature, and if the active has completely dissolved, additional active ingredient is added and the mixture is stirred another 24 h at room temperature. The percent solubility is recorded, and performance is compared with that of a standard agricultural solvent.

When the method outlined above is followed, two amine compositions, C10-38 and C12-26, perform as well as the applicable control in this test. See Table 6.

TABLE 6

Agricultural Solvent Testing

| Solvent | 2,4-D Acid | Imidacloprid | Trifluralin | Tebuconazole |
|---|---|---|---|---|
| C10-38 | 56.8 | — | — | 4.5 |
| C12-26 | 61.6 | <0.2 | 51.2 | 2.5 |

TABLE 6-continued

Agricultural Solvent Testing

| Solvent | 2,4-D Acid | Imidacloprid | Trifluralin | Tebuconazole |
|---|---|---|---|---|
| $C_{12}$-$C_{14}$ dimethylamide | 38.2 | 1.9 | 64.0 | 32.2 |
| N,N-dimethylcapramide | 42.7 | 4.0 | 67.1 | 38.0 |
| methyl laurate | 11.2 | 0.6 | 58.8 | 5.9 |
| methyl caprate/caprylate | 14.8 | 0.6 | 69.9 | 10 |
| aromatic hydrocarbon | 0.6 | 1.0 | 78.9 | 4.2 |
| N-methyl-2-pyrrolidone | 39.5 | 29.3 | 78 | 62.2 |

Agricultural Products: Anionic Emulsifiers

Anionic surfactant samples contain a relatively high amount of water (>20%) and are prepared as oil-in-water (EW) concentrates. These are tested against controls containing a standard surfactant or a blank. Enough is formulated to test two water hardnesses (34 ppm and 1000 ppm) for each of the three samples.

Sample Preparation:

Pyraflufen (97.8% active, 0.30 g) is combined and with Stepan® C-25 (methyl caprylate/caprate, 7.20 g), and N-methyl-2-pyrrolidone (1.20 g), and the mixture is stirred magnetically until dissolved. In a separate container, Toximul® 8242 (castor oil ethoxylate, POE 40, product of Stepan) 0.96 g), Ninex® MT-630F (fatty acid ethoxylate, POE 30, Stepan, 0.19 g), Ninex® MT-615 (fatty acid ethoxylate, POE 15, Stepan, 0.17 g), Aromatic 150 solvent (ExxonMobil, 0.37 g), and the anionic sample to be tested (0.71 g) are blended. If needed, the anionic sample is melted in an oven at 50-60° C. prior to combining with the other surfactants. When the pyraflufen has dissolved, the entire surfactant blend is added and magnetically stirred until homogeneous. Deionized water (0.90 g) is slowly added with mixing to prevent gelling. Turbidity changes are noted and recorded.

Control 1 Sample:

The same procedure is followed except that the anionic sample is replaced with Ninate® 60L (calcium alkylbenzenesulfonate, Stepan, 0.71 g).

Control 2 Sample:

No Ninate 60L (or anionic sample) is included, and the Aromatic 150 amount is increased to 1.08 g.

Emulsion Stability Testing

ASTM E1116-98 (2008) is modified as follows. Flat-bottomed, 100-mL graduated cylinders are charged with 34 ppm or 1000 ppm water (95 mL). A Mohr pipette is used to feed EW concentrate to each cylinder. Cylinders are stoppered and inverted ten times, then allowed to stand for 0.5, 1, and 24 h while recording stability at each time as type and % separation.

Spontaneity is recorded according to the following criteria: (1) poor: very thin emulsion cloud with major separation of oil droplets; (2) fair: thin emulsion cloud with minor separation of oil droplets; (3) good: thin emulsion cloud reaches the bottom of the cylinder without separation of any type; (4) excellent: thick emulsion cloud reaches the bottom of the cylinder without separation of any type.

Results are provided in Table 7. The three samples indicated below are rated "good" overall as an anionic surfactant.

TABLE 7

Performance as an Anionic Emulsifier: % Separation

| | 34 ppm water | | | 1000 ppm water | | |
|---|---|---|---|---|---|---|
| | Spont. | 1 h | 24 h | Spont. | 1 h | 24 h |
| Control 1 | G | <0.2 C | 1.3 C | G | <0.2 C | 1.3 C |
| Control 2 | F | 4 C | 4.4 C | F | 4 C | 4.4 C |
| C12-42 | F | 3 C | 3.1 C | F | 3 C | 3.3 C |
| C16-11 | F | 3.1 C | 4 C | F | 2.8 C | 3.6 C |
| C18-30 | F | 3.9 C | 3.5 C, 0.5 O | F– | 3.1 C | 3.6 C |

"C" denotes separation in the form of a cream, not a creamy oil or an oil.
"Tr" denotes trace of oil observed.
"O" denotes oil separated
"Spon." = spontaneity or bloom, rated as E (excellent), G (good), F (fair), P (poor).
Control 1 = native anionic;
control 2 = no anionic emulsifier.

Hard-Surface Cleaners: Aqueous Degreasers

This test measures the ability of a cleaning product to remove a greasy dirt soil from a white vinyl tile. The test is automated and uses an industry standard Gardner Straight Line Washability Apparatus. A camera and controlled lighting are used to take a live video of the cleaning process. The machine uses a sponge wetted with a known amount of test product. As the machine wipes the sponge across the soiled tile, the video records the result, from which a cleaning percentage can be determined. A total of 10 strokes are made using test formulation diluted 1:32 with water, and cleaning is calculated for each of strokes 1-10 to provide a profile of the cleaning efficiency of the product. The test sample is used as a component of different control formulations depending on whether it anionic, amphoteric, or nonionic.

Anionic Test Samples:

A neutral, dilutable all-purpose cleaner is prepared from propylene glycol n-propyl ether (4.0 g), butyl carbitol (4.0 g), sodium citrate (4.0 g), Bio-Soft® EC-690 ethoxylated alcohol (1.0 g, product of Stepan), test sample (0.29 g if 100% active material), and deionized water (to 100.0 g solution). The control sample for anionic testing replaces the test sample with Stepanol® WA-Extra PCK (sodium lauryl sulfate, Stepan, 1.0 g, nominally 30% active material).

Nonionic and Amphoteric Test Samples:

A neutral, dilutable all-purpose cleaner is prepared from propylene glycol n-propyl ether (4.0 g), butyl carbitol (4.0 g), sodium citrate (4.0 g), Stepanol WA-Extra PCK (sodium lauryl sulfate, 1.0 g), test sample (0.90 g if 100% active material), and deionized water (to 100.0 g solution). The control sample for nonionic/amphoteric testing replaces the test sample with Bio-Soft EC-690 (ethoxylated alcohol, 1.0 g, nominally 90% active material).

Soil Composition:

Tiles are soiled with a particulate medium (50 mg) and an oil medium (5 drops). The particulate medium is composed of (in parts by weight) hyperhumus (39), paraffin oil (1), used motor oil (1.5), Portland cement (17.7), silica 1 (8), molacca black (1.5), iron oxide (0.3), bandy black clay (18), stearic acid (2), and oleic acid (2). The oil medium is composed of kerosene (12), Stoddard solvent (12), paraffin oil (1), SAE-10 motor oil (1), Crisco® shortening, product of J.M. Smucker Co. (1), olive oil (3), linoleic acid (3), and squalene (3).

Five anionic (sulfonate) and three amphoteric (amidoamine, amine oxide) samples perform equal to the control in this test (see Tables 8 and 9).

TABLE 8

Control Runs for Gardner Straight Line Washability Test

| | Ave. % clean after 2, 4, 6, 8, or 10 swipes | | | | |
|---|---|---|---|---|---|
| | 2 | 4 | 6 | 8 | 10 |
| Control 3 | 54.6 | 61.4 | 64.3 | 68.4 | 72.2 |
| Control 4 | 52.5 | 58.2 | 59.5 | 60.9 | 63.3 |
| Control 6 | 51.2 | 57.6 | 62.7 | 62.6 | 66.0 |
| Control 11 | 53.0 | 61.0 | 63.6 | 64.6 | 66.2 |
| Control 17 | 54.7 | 63.7 | 64.6 | 66.1 | 69.6 |

TABLE 9

Gardner Straight-Line Washability

| Sample | Con. # | Compound class | Ave. % clean | | | | | Rating |
|---|---|---|---|---|---|---|---|---|
| | | | 2 | 4 | 6 | 8 | 10 | |
| | | Nonionic/Amphoteric Test Samples | | | | | | |
| C10-39 | 6 | amine oxide | 47.4 | 56.8 | 60.4 | 59.8 | 61.9 | equal |
| C16-9 | 11 | DMAPA amide | 48.0 | 53.9 | 60.1 | 62.2 | 64.7 | equal |
| UTG-12 | 4 | DMAPA amine oxide | 43.3 | 51.2 | 54.3 | 55.0 | 57.4 | equal |
| | | Anionic Test Samples | | | | | | |
| C10-21 | 3 | DMAPA AO sulfonate | 51.1 | 56.4 | 57.4 | 63.3 | 65.9 | equal |
| C12-21 | 11 | DMAPA AO sulfonate | 58.2 | 63.9 | 63.7 | 64.2 | 65.3 | equal |
| C12-42 | 11 | DMAPA sulfonate | 54.5 | 60.2 | 61.5 | 63.5 | 65.3 | equal |
| C18-30 | 17 | diDMAPA AO sulfonate | 55.3 | 59.2 | 64.1 | 65.9 | 66.2 | equal |
| C18-68 | 17 | diDMAPA sulfonate | 53.9 | 63.3 | 66.8 | 67.6 | 70.0 | equal |

Hard-Surface Cleaners: Foaming Glass and Window Cleaner

Control: Ammonyx® LO (lauramine oxide, 0.70 g, product of Stepan, nominally 30% active) and Bio-Terge® PAS-8S (2.00 g, sodium caprylyl sulfonate, product of Stepan, nominally 38% active) are combined with isopropyl alcohol (2.50 g) and diluted to 100 mL with deionized water.

Test formulation: Test sample (0.21 g if 100% active material) and Bio-Terge PAS-8S (2.00 g) are combined with isopropyl alcohol (2.50 g) and diluted to 100 mL with deionized water.

Method: The test formulation is evaluated for clarity; only clear formulations are evaluated in the low film/low streak test. The test measures the ability of the cleaner to leave a streak and film-free surface on a test mirror. The test formula is applied to a mirror in a controlled quantity and wiped with a standard substrate back and forth, leaving the spread product to dry. Once dry, the mirrors are inspected and evaluated by a two-person panel. Ratings of "better than," "equal" or "worse than" the control are assigned. The formulation used here is used to evaluate amphoteric and nonionic surfactants. Five test samples performed equal to the control (see Table 10).

TABLE 10

Overall Performance Equal to Control in Foaming Glass & Window Cleaner Test

| C12-28 | UTG-12 |
|---|---|
| MTG-12 | PUTG-12 |
| PMTG-12 | |

Cold-Water Cleaning Performance of Compaction Laundry Detergents

This method evaluates the overall cold-water (55° F.) cleaning performance of a laundry detergent formula comprising a concentrated blend of anionic and nonionic surfactants, a builder, $C_{16}$ MES, and an experimental sample. The formulations are prepared as described below. The experimental sample is tested for its ability to improve the overall cleaning performance relative to cocamide DEA.

Preparation of Concentrated Blend:

Deionized water (90% of the required total amount) is first combined and mixed at 50° C. with Bio-Soft® S-101 (dodecylbenzene sulfonic acid, 3.27 wt. %, product of Stepan). Sodium hydroxide (50% aq. solution) is added to pH 11 (about 24% of the total amount of 4 wt. % required). Citric acid (50% aq. solution, 6.2 wt. %) is added, followed by triethanolamine (3.45 wt. %). Bio-Soft® EC-690 (laureth-7, 90% actives, 27.8 wt. %, product of Stepan) is slowly added. The pH is adjusted to the 7.8 to 8.4 range, targeting 8.1 with the remaining aqueous sodium hydroxide solution. Sodium xylene sulfonate (40% actives, 4.30 wt. %) is added, followed by a preservative and the remaining deionized water (q.s. to 100 wt. %).

Preparation of an Ultra Laundry Detergent with $C_{16}$ MES and the Blend:

Deionized water (q.s. to 100 wt. %) is charged at 55-60° C. The concentrated blend prepared above (58.0 wt. %) is added while maintaining temperature between 50° C. and 60° C. The $C_{16}$ MES (87% actives, 10.34 wt. %) is slowly added and allowed to dissolve. The mixture is then allowed to cool to 35° C. The experimental sample or cocamide DEA standard (5.0 wt. %) is then added slowly and mixing continues until the batch is homogeneous.

Cold-Water Cleaning Evaluation:

Laundry detergent (30 g, see Part A) is charged to the laundry machine, followed by soiled/stained fabric swatches that are attached to pillowcases. Wash temperature: 55° F. Rinse: 55° F. The swatches are detached from pillowcases, dried, and ironed. Swatches are scanned to measure the L* a* b* values, which are used to calculate a soil removal index (SRI) for each type of swatch. Finally, the ΔSRI is calculated, which equals the experimental sample SRI minus the SRI of a pre-determined standard laundry detergent formula (or control). When |ΔSRI|≥1, differences are perceivable to the naked eye. If the value of ΔSRI is greater than or equal to 1, the sample is superior. If ΔSRI is less than or equal to −1, the sample is inferior. If ΔSRI is greater than −1 and less than 1, the sample is considered equal to the standard.

The following standard soiled/stained fabric swatches are used: dust sebum on cotton (DSC); beef tallow (BT); kaolin clay and wool fat on polyester (WFK 30C), grass on cotton (GC); blueberry on cotton (BC); cocoa on cotton (EMPA 112); and blood/ink/milk on cotton (EMPA 116). At least three of each kind of swatch are used per wash. Swatches are stapled to pillowcases for laundering, and extra pillowcases are included to complete a six-pound load.

The same procedure is used to launder all of the pillowcases/swatches, with care taken to ensure that water temperature, wash time, manner of addition, etc. are held constant for the cold-water wash process. When the cycle is complete, swatches are removed from the pillowcases, dried at low heat on a rack, and pressed briefly with a dry iron.

A Hunter LabScan® XE spectrophotometer is used to determine the L* a* b* values to calculate the SRI for every type of swatch, and the stain removal index (SRI) is calculated as follows:

$$SRI = 100 - \sqrt{(L*_{clean} - L*_{washed})^2 + (a*_{clean} - a*_{washed})^2 + (b*_{clean} - b*_{washed})^2}$$

$$\Delta SRI = SRI_{sample} - SRI_{standard}$$

Five test samples perform as well as or better than the control in the cold-water cleaning test (see Table 11).

TABLE 11

Performance in Cold-Water Cleaning:
|ΔSRI|Values v. Cocamide DEA in a $C_{16}$ Methyl Ester Sulfonate (MES) Formulation

| | ΔSRI values | | | | |
|---|---|---|---|---|---|
| test sample | C12-17 | C16-9 | C16-11 | C18-29 | UTG-12 |
| dust sebum on cotton (DSC) | −0.8 | −0.1 | 0.4 | −0.6 | −0.6 |
| beef tallow (BT) | 5.4 | 1.7 | 1.1 | 1.9 | −0.3 |
| pigment/lanolin (WFK 30C) | −0.3 | 0.7 | 0.5 | −0.5 | 0.2 |
| blueberry on cotton (BC) | 1.4 | −0.4 | 0.3 | 2.3 | −0.2 |

TABLE 11-continued

Performance in Cold-Water Cleaning:
|ΔSRI|Values v. Cocamide DEA in a $C_{16}$ Methyl Ester Sulfonate (MES) Formulation

| test sample | ΔSRI values | | | | |
|---|---|---|---|---|---|
| | C12-17 | C16-9 | C16-11 | C18-29 | UTG-12 |
| cocoa on cotton (EMPA 112) | 1.2 | 1.0 | 2.0 | 1.3 | 0 |
| blood/ink/milk on cotton (EMPA 116) | 0.8 | 0.7 | 1.6 | −0.4 | −0.7 |
| grass on cotton (GC) | 0.8 | −1.2 | −0.6 | 0.1 | −0.5 |
| overall rating | superior | good | superior | superior | good |

Booster for Bargain Laundry Detergent

This method evaluates the cleaning boosting ability of an experimental sample when used as an additive in a bargain laundry detergent formulation that contains neutralized dodecylbenzene sulfonic acid, a non-ionic surfactant such as an ethoxylated synthetic $C_{12}$-$C_{15}$ alcohol (7 EO), citric acid, monoethanolamine, triethanolamine, and a preservative. The experimental sample is tested for its ability to improve the overall cleaning performance at 1% solids level relative to Ammonyx® LO (lauramine oxide, standard booster, product of Stepan). Laundry detergent formula (46 g) is charged to the laundry machine, followed by soiled/stained fabric swatches that are attached to pillowcases. Wash temperature: 90° F. Rinse: 70° F. The swatches are detached from pillowcases, dried, and ironed.

The bargain laundry detergent with booster is prepared from sodium hydroxide-neutralized dodecylbenzene sulfonic acid (Bio-Soft® S-101, 33.9% actives, 41.3 wt. %), Bio-Soft® N25-7 (fatty alcohol ethoxylate, product of Stepan, 5.00 wt. %), booster (either the experimental sample or Ammonyx LO, which is 30% actives, 3.33 wt. %, citric acid (50% aq. solution, 1.00 wt. %), monoethanolamine (1.00 wt. %), triethanolamine (1.00 wt. %), and deionized water plus preservative (balance to 100 wt. %).

The formulation is made by charging 90% of the total amount of water at 50° C., then adding in order, with mixing, citric acid solution, monoethanolamine, triethanolamine, neutralized sulfonic acid, Bio-Soft N25-7, and booster. The pH is adjusted to 9.5 with 25% aq. NaOH solution, and then preservative and the balance of the water are added.

The following standard soiled/stained fabric swatches are used: dust sebum on cotton (DSC); dust sebum on cotton/polyester (DSCP); beef tallow (BT); clay on cotton (CC); clay on cotton/polyester (CCP); grass on cotton (GC); red wine on cotton (RWC); blueberry on cotton (BC); coffee on cotton (COFC); cocoa on cotton (EMPA 112); blood/ink/milk on cotton (EMPA 116); and make-up on cotton (EMPA 143). At least three of each kind of swatch are used per wash. Swatches are stapled to pillowcases for laundering, and extra pillowcases are included to complete a six-pound load.

The same procedure is used to launder all of the pillowcases/swatches, with care taken to ensure that water temperature, wash time, manner of addition, etc. are held constant for the cold-water wash process. When the cycle is complete, swatches are removed from the pillowcases, dried at low heat on a rack, and pressed briefly with a dry iron.

A Hunter LabScan® XE spectrophotometer is used to determine the L* a* b* values to calculate the SRI for every type of swatch, and the stain removal index (SRI) is calculated as described above.

As shown in Table 12, one of the test samples (Mix-46) provides superior performance and one sample (Mix-73) provides equal performance versus the control when evaluated as boosters for bargain laundry detergents.

TABLE 12

Performance as a Booster for a Bargain Detergent Formulation:
|ΔSRI| Values versus Ammonyx LO (Lauramine Oxide)

| | DSC | DSCP | BT | CC | CCP | GC | RWC | BC | COFC | 112 | 116 | 143 |
|---|---|---|---|---|---|---|---|---|---|---|---|---|
| Performance Superior to Control Sample: | | | | | | | | | | | | |
| Mix-46 | 0.9 | 1.4 | −0.3 | 0.7 | 0.4 | 1.0 | 1.6 | 0.1 | −0.4 | −0.5 | 0.7 | −0.2 |
| Performance Equal to Control Sample: | | | | | | | | | | | | |
| Mix-73 | 1.0 | 0.3 | −2.9 | 0.0 | 1.0 | 1.0 | 1.0 | 0.2 | −0.2 | 0.1 | 1.2 | 1.2 |

Personal Care: Cleansing Application

Viscosity and mechanical shake foam tests are used to assess the likely value of a particular surfactant as a secondary surfactant in cleansing applications for personal care.

All experimental samples are evaluated for their performance versus a control (either cocamide MEA or cocamidopropylbetaine).

Viscosity curves are generated by preparing aqueous solutions of the test material or the control with 12% active sodium laureth(1) sulfate (SLES-1), then measuring viscosity by means of a Brookfield DV-1+ viscometer. The active contents of test material are 1.5% if the material is an amidoamine, and 3% if the material is an amidoamine oxide. Sodium chloride is added incrementally (1-3 wt. %) and viscosity is recorded as a function of increasing NaCl concentration. A "good" result is a curve that shows a viscosity build comparable to the control sample. A "superior" rating indicates that the sample builds viscosity substantially more rapidly than the control.

Foaming properties are evaluated using a mechanical shake foam test. Aqueous solutions composed of 12% active SLES-1 and the test material or control (1.5% active content if material is an amidoamine, 3% active content if material is an amidoamine oxide) are prepared. Sample solutions calculated at 0.2% total surfactant active are thereafter made from the aqueous solutions using 25° C. tap water. A 100.0-g portion of the solution is carefully transferred to a 500-mL graduated cylinder. Castor oil (2.0 g) is added. The cylinder is stoppered and mechanically inverted ten times, then allowed to settle for 15 s. Foam height is recorded. After 5 min., foam height is recorded again. The experiment is repeated without the castor oil. In one set of experiments, the cleansing base contains SLES-1 in both the experimental and control runs. In a second set of experiments, the cleansing base contains another widely used anionic surfactant, i.e., a mixture of sodium methyl 2-sulfolaurate and disodium 2-sulfolaurate, instead of SLES-1. A "good" result is recorded when the solution containing the test material results in foam heights that are within +/−25 mL of the control runs. Results >25 mL of the control garner a superior rating; results <25 mL of the control are rated inferior.

Ten test materials, identified in Table 13, show at least good overall performance in the viscosity and foam tests.

TABLE 13

Personal Care--Cleansing Application
Viscosity and Shake Foam Test Results

| Sample | Viscosity Build | Foam Tests | Sample | Viscosity Build | Foam Tests |
|---|---|---|---|---|---|
| C12-17 | inferior[1] | good[1] | MTG-12 | inferior[2] | superior[2] |
| C12-20 | good[2] | good[2] | PMTG-5 | good[1] | good[1] |
| C16-9 | good[1] | good[1] | PMTG-12 | good[2] | good[2] |
| Mix-26 | good[1] | good[1] | UTG-5 | good[1] | good[1] |
| MTG-5 | superior[1] | good[1] | PUTG-12 | good[2] | good[2] |

[1]Control = cocamide MEA;
[2]Control = cocamidopropyl betaine

Personal Care/Antibacterial Handsoap:
Method to Determine Foam Enhancement Benefit Foam volume, which signals "clean" to consumers, is a desirable attribute in an antibacterial handsoap. Because cationic antibacterial actives are not compatible with anionic surfactants (the best foamers), achieving sufficient foam volume with them is challenging. The method below identifies surfactants that provide more foam volume than cocamidopropylbetaine (actives/actives basis) in an antibacterial handsoap base. Formulation: deionized water (q.s. to 100 wt. %), cocoglucoside (3.0 wt. %), lauramine oxide (3.0 wt. %), benzalkonium chloride (0.1 wt. %), and test molecule or cocamidopropylbetaine (3.0 wt. %).

Solutions are prepared by combining ingredients in the order prescribed above, stirring with a stir bar or mixing gently using an overhead stirrer or manually using a spatula. Heat may be applied if the test molecule is a solid at room temperature. Mixing is maintained to ensure a homogenous solution. The pH is adjusted to 6.5+/−0.5.

Test and control solutions are compared, with and without 2% castor oil, at 0.2% total surfactant active concentration (2.22 g solution to 100 mL with tap water from Lake Michigan, ~150 ppm Ca/Mg hardness) for foam volume using the cylinder inversion test. Initial and delayed (5 min.) measurements are taken.

Rating system: Superior: a result >25 mL over the cocamidopropylbetaine control in both oil and no-oil systems. Good: a result within 25 mL of the cocamido-propylbetaine control in both oil and no-oil systems. Inferior: a result >25 mL below that of the cocamidopropylbetaine control in both oil and no-oil systems.

Compared with the controls, the eleven test materials identified in Table 14 all show good overall performance in the antibacterial handsoap tests:

TABLE 14

Good Performance in Antibacterial Handsoap

| C12-20 | C18-29 | UTG-5 | MTG-12 |
| C12-21 | Mix-29 | UTG-12 | PMTG-5 |
| C16-11 | C18-30 | PUTG-5 | |

Oil Field Products: Paraffin Dispersants
Asphaltenes Screening Test

During acid stimulation of an oil well, a blend of HCl, HF, and corrosion inhibitor is pumped down a well, allowed to stand, and then pumped out. During the transfer of the acid, small amounts of iron chloride are developed in the acid solution. Once the acid blend dissolves scales and deposits in the well bore, crude oil begins to flow and mixes with the acid solution in the well. The crude oil can solidify after acidizing, and asphaltenes have been associated with the problem. Thus, dispersants are commonly added to the acid to prevent the solidification.

Test Method:

A stock solution of iron-contaminated acid is made by adding 1% $FeCl_3$ to a 15% HCl acid solution. The sample dispersant to be tested (0.2 wt. %) is added to the acid stock solution (7.5 mL). A 15-mL vial is charged with the acid/dispersant mixture and crude oil (2.5 mL), and the vial is shaken vigorously for 30 s. The initial appearance is recorded. After standing at room temperature for 1 h, the appearance is again noted. The vial is placed in an oven (50° C.) for 24 h and its appearance is recorded. The vial is allowed to cool to room temperature and appearance is again noted. Finally, after 24 h at room temperature, appearance is again noted. A blank sample containing crude oil and acid solution but no dispersant is run. A control sample containing soy amidoamine trimethylammonium chloride as the dispersant is also run. Yet another sample is run containing a 1:1 mixture of test dispersant and soy amidoamine trimethylammonium chloride.

Three samples provide performance equal to the control in this test, while MTG-15 demonstrates superior performance (Table 15).

TABLE 15

Good Performance in Oilfield Paraffin Dispersants

| C18-26 | C18-29 | PMTG-5 |
| MTG-5* | | |

*superior performer

Gas Well Foamers: Batch Dynamic Test

In this procedure, test surfactant, brine, and/or condensate are added to a column and then agitated with nitrogen to produce foam. The wt. % of foam carried over the column after 5 min. is a measure of the test sample's performance. Results are collected as a function of brine composition, concentration of surfactant, and percent condensate present in the solution.

Brines are prepared at 12.5% and 25% total dissolved solids (TDS). The brines are an 80:20 ratio of NaCl to $CaCl_2$. The density of the 12.5% TDS is 1.087 g/mL and the density of the 25% TDS is 1.184 g/mL. Brine solutions are filtered to eliminate particulates.

Surfactant samples are tested at 5000, 2000, 1000, and 500 parts per million of actives in each of the brine solutions listed above. A test solution consists of brine, surfactant, and condensate when applicable. The equation below indicates how much surfactant is needed based on actives level and the density of the brine used.

$$\text{Surfactant (g)} = \frac{\left[\frac{\text{desired ppm}}{1000}\right]}{0.45 \text{ actives}} \times \frac{\left[\frac{\text{Total Sol'n(g)}}{\text{Density of Brine (g/mL)}}\right]}{1000}$$

This sample calculation shows how much of a 45% active surfactant is needed to make a 5000 ppm solution in 12.5% TDS brine:

$$\frac{\left[\frac{5000 \text{ ppm}}{1000}\right]}{0.45 \text{ actives}} \times \frac{\left[\frac{238.053 \text{ g}}{1.087 \text{ g/mL}}\right]}{1000} =$$

2.43 g of Surfactant into 238.053 g of 12.5% TDS brine

The 5000 ppm solution is used to make a 2000 ppm solution, which is diluted to make a 1000 ppm solution, and so on. When condensate is included, the desired active level in the brine should be such that the active level in the total test solution remains constant with the varying amounts of condensate present. For example, when making a 5000 ppm solution with 10% condensate, the brine/surfactant solution will actually be 5556 ppm so that the solution plus condensate will be ~5000 ppm. When testing how well a product handles condensate, either 10% or 20% is added to a solution. This is done for both brine solutions at every concentration level.

The condensate used is a low-aromatic mineral spirit, Exxsol® D-40 (d=0.7636 g/mL), product of ExxonMobil. The desired amount of condensate is added to the column after the brine/surfactant solution is added. Nitrogen is fed through a glass frit in the bottom of the column and a mass-flow controller is used to feed 14 standard cubic feet per hour. DataStudio (from Pasco) software and a balance are used to measure the amount of foam collected. Weight is recorded every second over the course of a 10-minute run. The % of liquid carried over as foam after 5 min. for each brine solution at each % condensate level is reported in Table 16.

As shown in Table 16, four of the test samples perform as well or better than the control when evaluated as potential gas well foamers.

TABLE 16

Performance in Gas Well Foamers

| % TDS brine | % Condensate | Conc, ppm | % Carry Over at 5 min. | | | |
|---|---|---|---|---|---|---|
| | | | C10-39 | C12-28 | PUTG-12 | MTG-12 |
| 12.5 | 0 | 500 | 0 | 50 | 36 | 27 |
| 12.5 | 10 | 500 | 38 | 63 | 24 | 44 |
| 12.5 | 20 | 500 | 43 | 55 | 13 | 43 |
| 25.0 | 0 | 500 | 52 | 57 | 28 | 17 |
| 25.0 | 10 | 500 | 0 | 55 | 23 | 31 |
| 25.0 | 20 | 500 | 0 | 39 | 7 | 15 |
| 12.5 | 0 | 1000 | 28 | 68 | 63 | 42 |
| 12.5 | 10 | 1000 | 49 | 76 | 62 | 43 |
| 12.5 | 20 | 1000 | 57 | 63 | 51 | 36 |
| 25.0 | 0 | 1000 | 64 | 62 | 40 | 29 |
| 25.0 | 10 | 1000 | 32 | 54 | 46 | 46 |
| 25.0 | 20 | 1000 | 0 | 43 | 27 | 32 |
| 12.5 | 0 | 2000 | 73 | 90 | 70 | 56 |
| 12.5 | 10 | 2000 | 82 | 79 | 69 | 63 |
| 12.5 | 20 | 2000 | 84 | 75 | 61 | 49 |
| 25.0 | 0 | 2000 | 79 | 80 | 62 | 37 |
| 25.0 | 10 | 2000 | 56 | 57 | 57 | 34 |
| 25.0 | 20 | 2000 | 21 | 44 | 39 | 44 |
| 12.5 | 0 | 5000 | 85 | 92 | 80 | 73 |
| 12.5 | 10 | 5000 | 89 | 85 | 69 | 62 |
| 12.5 | 20 | 5000 | 82 | 73 | 60 | 60 |
| 25.0 | 0 | 5000 | 81 | 84 | 67 | 54 |
| 25.0 | 10 | 5000 | 87 | 58 | 52 | 41 |
| 25.0 | 20 | 5000 | 47 | 46 | 41 | 39 |
| Rating | | | equal | superior | equal | equal |

Performance as a Paint Additive

Formulations:

Titanium dioxide slurry (Dupont Ti-Pure® R746) is charged to a container, followed by deionized water and propylene glycol, and the contents are mixed (500 rpm). Latex (49% solids) and preservative (Acticide® GA, product of Thor) are added. Thickener (Acrysol™ SCT-275, product of Dow, 0.3%) is slowly charged below the liquid surface by syringe. The pH is adjusted to 9.0 using ammonium hydroxide solution. The batch is mixed for 30 min. and then allowed to stand for at least 2 h. The batch is remixed gently, and a portion (240 g) is transferred to a 400-mL beaker. Solvent ($C_{18}$ amide, 0.5% VOC, EPA Method 24, 5 wt. % based on latex solids) and derivative (1% active based on latex solids) are added and mixed at 650 rpm. Viscosity is adjusted to an initial KU of 90 with more thickener. The paint is covered and final KU is measured after 24 h. Its value falls within the range of 93-100 KU and varies from the original measurement by no more than 5 KU.

Example formulation: $TiO_2$ (solids basis): 24.35 wt. %; water: 46.39 wt. %; propylene glycol 2.59 wt. %; latex (solids basis) 22.76%; ammonium hydroxide: 0.04 wt. %; preservative: 0.10 wt. %; control additive (solvent): 1.14 wt. %; derivative (56% active): 0.40 wt. %; thickener: 2.23 wt. %. PVC: 22.1%. VOC: <50 g/L. Final KU: 98.6.

Wet Scrub Resistance/ASTM 2486 Modified:

Wet scrub resistance based on a modified version of ASTM-2486-00, method B; modified to % weight loss, is performed for each paint formulation. Paints are applied to Leneta P-121-10N plastic panels using a 13-cm wide, 10-mil wet film applicator and dried under ambient conditions for five days prior to testing. The coated panels are then cut into strips (16.5 cm×5.7 cm, two per drawdown). The strips are weighed prior to testing. Two samples at a time are placed on a Gardner Company scrub tester with approximately a 2" gap between the samples and taped to secure panels to the machine. A spacer is placed over the samples to maintain the scrub brush pathway and further secure the samples. A scrub brush (8 cm×3 cm), preconditioned in room temperature water, is inserted into the holder. Scrub compound (10 g, supplied by Leneta Company as "ASTM-2486 scrub compound") is applied evenly to the brush. Water (5 g) is placed into the gap between the samples. Samples are tested to 1200 cycles. Additional scrub compound (10 g) and water (5 g) are reapplied every 300 cycles. The strips are then rinsed under tepid water and dried for 24 h. The strips are reweighed and the % coating removed is determined.

Gloss Determination—60°/20°—ASTM D523

Paints are applied to Leneta P-121-10N plastic panels using a wet film applicator (13 cm×10 mil) and dried under ambient conditions for 5 days prior to testing. Gloss is measured with an ASTM accepted glossmeter (Gardco).
Results:
Two of the samples tested perform as well as the control surfactants, while three are superior as a paint additive (see Table 17).

TABLE 17

Performance as a Latex Paint Additive

| | 60° gloss | 20° gloss | % coating removed, scrub | rating |
|---|---|---|---|---|
| Control 1 | 51.2 | 9.9 | 1.9 | — |
| C12-17 | 51.1 | 10.4 | 1.6 | superior |
| Control 1 | 56.5 | 12.3 | 1.92 | — |
| Control 2 | 60.2 | 14.8 | 1.81 | — |
| C10-39 | 67.5 | 20.1 | 1.86 | equal |
| C12-28 | 67.8 | 21.2 | 1.91 | equal |
| Control 1 | 55.7 | 12.4 | 2.30 | — |
| Mix-46 | 68.0 | 22.1 | 2.62 | superior |
| Control 1 | 47.7 | 8.7 | 2.12 | — |
| Mix-73 | 68.3 | 21.4 | 2.42 | superior |

Performance as a Foamer or Foam Additive for Specialty Foamer Applications

Specialty foamer applications include (among others) gypsum, concrete, and fire-fighting foams. The tests below evaluate foam stability when the sample is used as the primary foamer and also evaluate the sample's performance as an additive when used as a foam stabilizer, enhancer, or destabilizer.

Particularly for gypsum, for which set-up times are rapid on commercial production lines, a desirable foam additive helps to control the coalescence of the bubble to provide a larger bubble within a prescribed time frame. Preferably, destabilization of the foam occurs at the end of the first minute in the tests below. These compositions are identified as "good" performers as gypsum foam destabilizers in Table 18 because they allow this balance to be struck effectively.

Two of the samples, C12-20 and UTG-12, also exhibit good performance as "stand-alone" foamers.

Foam Stability: Drainage Method

Surfactant solutions (0.4 wt. % active material) are prepared by mixing surfactant with waters having varying hardnesses (342 ppm hard water or 1000 ppm CaSO₄ water). Surfactant solution (100 mL) is carefully transferred to a stainless-steel mixing cup, then mixed at high speed (27K rpm) using a Hamilton Beach mixer for 10 s. The contents are quickly poured into a 100-mL graduated cylinder to the 100-mL mark, and a stopwatch is immediately started. The amount of liquid settling in the cylinder is recorded every 15 s for 4 min. Less liquid drained indicates greater foam stability.

Foam Stability: Foam Half Life

A sample of surfactant solution prepared as described above (100 g) is mixed at high speed for 30 s. The mixture is quickly poured into a 1000-mL graduated cylinder and a stopwatch is immediately started. Initial foam height is recorded. When 50 mL of liquid appears in the cylinder, the time and foam height are recorded as the foam half life (in seconds) and foam height at half life (in mL), respectively.

TABLE 18

Good Performance in Gypsum Applications

| Stand-Alone Foamer | |
|---|---|
| C12-20 | UTG-12 |
| Foam Additive | |
| C10-20 | UTG-12 |
| C12-20 | PUTG-12 |

The preceding examples are meant only as illustrations. The following claims define the invention.

We claim:
1. A fatty amidoamine having the formula:

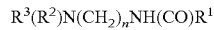

wherein $R^1$ is $-C_9H_{16}-R^4$ or $-C_{16}H_{30}-(CO)NH(CH_2)_nN(R^2)R^3$; each of $R^2$ and $R^3$ is independently substituted or unsubstituted alkyl, aryl, alkenyl, oxyalkylene, or polyoxyalkylene; $R^4$ is hydrogen or $C_1$-$C_7$ alkyl; and n=2-8; wherein when $R^4$ is $C_1$-$C_7$ alkyl, the fatty amidoamine has at least 1 mole % of trans-$\Delta^9$ unsaturation.

2. A derivative made by one or more of sulfonating, sulfitating, or oxidizing the amidoamine of claim 1.

3. The amidoamine of claim 1 wherein the fatty amidoamine has at least 50 mole % of trans-$\Delta^9$ unsaturation.

4. The amidoamine of claim 1 wherein (i) $R^2$ and $R^3$ are methyl and n is 3; (ii) $R^2$ and $R^3$ are ethyl and n is 3; (iii) $R^2$ and $R^3$ are methyl and n is 2; or (iv) $R^2$ and $R^3$ are methyl and n is 4.

5. A fatty amidoamine comprising a reaction product of an aminoalkyl-substituted tertiary amine with (a) a modified triglyceride made by self-metathesis of a natural oil; or (b) an unsaturated triglyceride made by cross-metathesis of a natural oil with an olefin.

6. The amidoamine of claim 5 wherein the aminoalkyl-substituted tertiary amine is selected from the group consisting of N,N-dimethyl-1,3-propanediamine (DMAPA), N,N-diethyl-1,3-propanediamine, N,N-dimethyl-1,2-ethanediamine, and N,N-dimethyl-1,4-butanediamine.

7. A derivative made by one or more of sulfonating, sulfitating, or oxidizing the amidoamine of claim 5.

8. The amidoamine of claim 5 wherein the natural oil is selected from the group consisting of soybean oil, palm oil, rapeseed oil, algal oil, and mixtures thereof.

9. The amidoamine of claim 5 wherein the olefin is a $C_2$-$C_8$ α-olefin or a $C_4$-$C_9$ internal olefin.

10. A laundry detergent formulation comprising the amidoamine of claim 1.

11. A laundry detergent formulation comprising the amidoamine derivative of claim 2.

12. A laundry detergent formulation comprising the amidoamine of claim 5.

13. A laundry detergent formulation comprising the amidoamine derivative of claim 7.

* * * * *